US008609108B2

(12) United States Patent
Le Butt et al.

(10) Patent No.: US 8,609,108 B2
(45) Date of Patent: Dec. 17, 2013

(54) **GAMMA-GLUTAMYL TRANSPEPTIDASE ATTENUATED *FRANCISELLA***

(75) Inventors: Helen Le Butt, Salisbury (GB); Phillip Matthew Ireland, Salisbury (GB); Petra Claire Farquar Oyston, Salisbury (GB)

(73) Assignee: The Secretary of State for Defence (GB)

( * ) Notice: Subject to any disclaimer, the term of this patent is extended or adjusted under 35 U.S.C. 154(b) by 0 days.

(21) Appl. No.: 13/264,175

(22) PCT Filed: Apr. 14, 2010

(86) PCT No.: PCT/GB2010/000743
§ 371 (c)(1),
(2), (4) Date: Oct. 13, 2011

(87) PCT Pub. No.: WO2010/119245
PCT Pub. Date: Oct. 21, 2010

(65) Prior Publication Data
US 2012/0107360 A1    May 3, 2012

(30) Foreign Application Priority Data

Apr. 14, 2009   (GB) ................... 0906234.0

(51) Int. Cl.
| A61K 39/02 | (2006.01) |
|---|---|
| A61K 39/38 | (2006.01) |
| A61K 48/00 | (2006.01) |
| A01N 63/00 | (2006.01) |
| C12N 1/36 | (2006.01) |

(52) U.S. Cl.
USPC ... 424/200.1; 424/93.2; 424/93.4; 424/235.1; 424/234.1; 424/184.1; 435/245

(58) Field of Classification Search
None
See application file for complete search history.

(56) References Cited

U.S. PATENT DOCUMENTS

| | | |
|---|---|---|
| 3,148,120 A | 9/1964 | Otto |
| 4,235,871 A | 11/1980 | Papahadjopoulos et al. |
| 4,235,877 A | 11/1980 | Fullerton |
| 4,501,728 A | 2/1985 | Geho et al. |
| 4,837,028 A | 6/1989 | Allen |
| 4,912,094 A | 3/1990 | Myers et al. |
| 5,019,369 A | 5/1991 | Presant et al. |
| 5,066,596 A | 11/1991 | Manning et al. |
| 5,187,074 A | 2/1993 | Treiber et al. |
| 5,192,668 A | 3/1993 | Treiber et al. |
| 5,278,302 A | 1/1994 | Caruthers et al. |
| 5,308,854 A | 5/1994 | Hoffman, Jr. et al. |
| 5,413,999 A | 5/1995 | Vacca et al. |
| 5,476,874 A | 12/1995 | Hungate et al. |
| 5,502,060 A | 3/1996 | Thompson et al. |
| 5,578,597 A | 11/1996 | Spector et al. |
| 5,663,169 A | 9/1997 | Young et al. |
| 5,666,153 A | 9/1997 | Copeland |
| 5,703,055 A | 12/1997 | Felgner et al. |
| 5,846,978 A | 12/1998 | Coburn et al. |
| 5,951,987 A | 9/1999 | Cherwonogrodzky et al. |
| 6,261,568 B1 | 7/2001 | Gicquel et al. |
| 6,268,171 B1 | 7/2001 | Meyer et al. |
| 6,303,347 B1 | 10/2001 | Johnson et al. |
| 6,350,454 B1 | 2/2002 | Thune |
| 6,406,705 B1 | 6/2002 | Davis et al. |
| 6,444,210 B1 | 9/2002 | Kournikakis et al. |
| 6,444,445 B2 | 9/2002 | Nikolich et al. |
| 6,444,804 B1 | 9/2002 | Lam et al. |
| 6,544,518 B1 | 4/2003 | Friede et al. |
| 6,552,006 B2 | 4/2003 | Raz et al. |
| 6,558,670 B1 | 5/2003 | Friede et al. |
| 6,764,840 B2 | 7/2004 | Johnson et al. |
| 7,087,586 B2 | 8/2006 | Filion et al. |
| 7,157,436 B2 | 1/2007 | Phillips et al. |
| 7,199,228 B2 | 4/2007 | Phillips et al. |
| 7,200,531 B2 | 4/2007 | Phillips et al. |
| 7,371,734 B2 | 5/2008 | Phillips et al. |
| 7,399,756 B2 | 7/2008 | Jomaa et al. |
| 7,588,744 B1 | 9/2009 | Sylvester |
| 7,592,326 B2 | 9/2009 | Karaolis |
| 7,635,686 B2 | 12/2009 | Phillips et al. |
| 7,662,792 B2 | 2/2010 | Phillips et al. |
| 8,198,430 B2 | 6/2012 | Prior et al. |
| 8,323,664 B2 | 12/2012 | Mitchell et al. |
| 2001/0024653 A1 | 9/2001 | Gicquel et al. |
| 2003/0022226 A1 | 1/2003 | Hooper et al. |
| 2004/0087555 A1 | 5/2004 | Belmant et al. |

(Continued)

FOREIGN PATENT DOCUMENTS

| EP | 0250614 | 1/1988 |
|---|---|---|
| EP | 0362278 | 4/1990 |

(Continued)

OTHER PUBLICATIONS

Ramakrishnan. In: Abstracts of the 104th ASM General Meeting, New Orleans, LA, abstract # D-178, May 25, 2004).*
"*Francisella tularensis*," Poster presented at ASM Meeting, Baltimore, MD, Mar. 20-23, 2005, 11 pgs.
Genbank Accession No. AASP01000000.1, *Francisella tularensis* subsp. holarctica FSC200, whole genome shotgun sequence, Jan. 17, 2007.
Search Report dated Aug. 3, 2011 in Application No. GB10000743.
Search Report dated Aug. 7, 2009 in Application No. GB0906234.0.
Search Report dated Aug. 13, 2010 in Application No. GB1006165.3.
"Tularemia," MedlinePlus Medical Encyclopedia. Located at http://www.nlm.nih.gov/medlineplus/ency/article/000856.htm, Jun. 28, 2011, 3 pages.
Agarwal et al., "Antisense therapeutics: is it as simple as complementary base recognition?" Abstract Only, Molecular Medicine Today, 2000, 6: 72-81.

(Continued)

*Primary Examiner* — S. Devi
(74) *Attorney, Agent, or Firm* — Kilpatrick Townsend & Stockton LLP

(57) ABSTRACT

The present invention relates to a mutated *Francisella* bacterium, wherein the ggt gene is silenced or deleted; pharmaceutical compositions comprising the same, in particular, vaccine compositions, and use of the bacterium and compositions for treatment and/or prophylaxis, and in particular, the treatment or prophylaxis of tularemia.

18 Claims, 4 Drawing Sheets

(56) References Cited

U.S. PATENT DOCUMENTS

| | | | |
|---|---|---|---|
| 2006/0218086 A1 | 9/2006 | Campbell et al. | |
| 2006/0280759 A1* | 12/2006 | Titball et al. | 424/234.1 |
| 2007/0066801 A1 | 3/2007 | Engler et al. | |
| 2007/0128225 A1 | 6/2007 | Prior et al. | |
| 2007/0264233 A1 | 11/2007 | Michell et al. | |
| 2007/0292386 A9 | 12/2007 | Campbell et al. | |
| 2008/0207568 A1 | 8/2008 | Belmant | |
| 2009/0087456 A1 | 4/2009 | Eyles et al. | |
| 2009/0196887 A1 | 8/2009 | Morita et al. | |
| 2010/0021501 A1 | 1/2010 | Mitchell et al. | |
| 2010/0047283 A1 | 2/2010 | Michell et al. | |
| 2010/0080828 A1 | 4/2010 | Prior et al. | |
| 2010/0119524 A1 | 5/2010 | Ulaeto et al. | |
| 2010/0204184 A1 | 8/2010 | Montero et al. | |
| 2012/0082698 A1* | 4/2012 | Conlan et al. | 424/234.1 |
| 2013/0122573 A1 | 5/2013 | Mitchell et al. | |

FOREIGN PATENT DOCUMENTS

| | | |
|---|---|---|
| EP | 0109942 | 3/1991 |
| EP | 468520 | 1/1992 |
| EP | 671948 | 8/1997 |
| EP | 689454 | 9/1997 |
| EP | 2123285 | 11/2009 |
| GB | 2220211 | 1/1990 |
| GB | 2321103 | 7/1998 |
| GB | 0625587 | 12/2007 |
| GB | 2445028 | 6/2008 |
| GB | 0906234.0 | 4/2009 |
| GB | 2469565 | 10/2010 |
| RU | 2240822 | 4/2004 |
| WO | 8808430 | 11/1988 |
| WO | 8809797 | 12/1988 |
| WO | 9111172 | 8/1991 |
| WO | 9213871 | 1/1992 |
| WO | 9311791 | 6/1993 |
| WO | 9402518 | 2/1994 |
| WO | 9421292 | 9/1994 |
| WO | 9514026 | 5/1995 |
| WO | 9517210 | 5/1995 |
| WO | 9526204 | 10/1995 |
| WO | 9633739 | 10/1996 |
| WO | 9741234 | 11/1997 |
| WO | 9815287 | 4/1998 |
| WO | 9850399 | 11/1998 |
| WO | 9855148 | 12/1998 |
| WO | 9856414 | 12/1998 |
| WO | 9964301 | 12/1999 |
| WO | 0000462 | 1/2000 |
| WO | 0126683 | 4/2001 |
| WO | 0146127 | 6/2001 |
| WO | 0158485 | 8/2001 |
| WO | 0218600 | 3/2002 |
| WO | 02060935 | 8/2002 |
| WO | 03068151 | 8/2003 |
| WO | 03102191 | 12/2003 |
| WO | 2004004654 | 1/2004 |
| WO | 2004084935 | 10/2004 |
| WO | 2004098491 | 11/2004 |
| WO | 2005013918 | 2/2005 |
| WO | 2005021708 | 3/2005 |
| WO | 2005054258 | 6/2005 |
| WO | 2005063802 | 7/2005 |
| WO | 2006067635 | 6/2006 |
| WO | 2006103568 | 10/2006 |
| WO | 2006111019 | 10/2006 |
| WO | 2006131752 | 12/2006 |
| WO | 2007028985 | 3/2007 |
| WO | 2007034166 | 3/2007 |
| WO | 2007097789 | 8/2007 |
| WO | 2008012538 | 1/2008 |
| WO | 2008075075 | 6/2008 |
| WO | 2010086617 | 8/2010 |
| WO | 2010119245 | 10/2010 |

OTHER PUBLICATIONS

Agarwal et al., "Medicinal chemistry and therapeutic potential of CpG DNA," Abstract Only, Trends in Mol. Med., 2002, 8: 114-121.

Alkhuder et al., "Glutathione Provides a Source of Cysteine Essential for Intracellular Multiplication of *Francisella tularensis*," PLoS Pathogens, 2009, 5:1-11.

Altschul et al., "Basic local alignment search tool," Journal of Molecular Biology, 1990, 215:403-410.

Altschul et al., "Gapped BLAST and PSI-BLAST: a new generation of protein database search programs," Nucleic Acids Research, 1997, 25(17):3389-3402.

Ascher et al., "Modulation of delayed-type hypersensitivity and cellular immunity to microbial vaccines: effects of cyclophosphamide on the immune response to tularemia vaccine." Clin. Exp. Immunology, 1980, 41:225-226.

Ascher et al., "Modulation of Delayed-Type Hypersensitivity and Cellular Immunity to Microbial Vaccines; Effects of Cyclophosphamide on the Immune Response to Tularemia Vaccine," Infection and Immunity, 1977, 18(2):318-323.

Atkins et al., "Characterisation of an acapsular mutant of *Burkholderia pseudomallei* identified by signature tagged mutagenesis," Journal Medical Microbiology, 2002, vol. 51(7):539-547.

Atlas, "Handbook of Microbiological Media," Thayer-Martin Agar, Modified; erd Ed., CRC Press, FLA, 2004, pp. 1365-1369.

Barker et al., "Basis for the Failure of *Francisella tularensis* Lipopolysaccharide to prime human Polymorphonuclear leukocyte," Infection and Immunity, 2006, 74(6):3277-3284.

Beélanger et al., "Functional analysis of genes responsible for the synthesis of the B-band O-antigen of *Pseudomonas aeruginosa* serotype 06 lipopolysaccharide," Microbiology, 1999, 145:3505-3521.

Boggs et al., "Characterization and modulation of immune stimulation by modified oligonucleotides," Antisense and Nucl. Acid Drug Dev., 1997, 7:461-471.

Bosio et al., "Active suppression of the pulmonary immune response by *Francisella tularensis* Schu4," Journal of Immunology, 2007, 178:4538-4547.

Bowie et al., "Deciphering the Message in Protein Sequences: Tolerance to Amino Acid Substitutions," Science, Mar. 16, 1990, 247:1306-1310.

Broekhuijsen et al., "Genome-Wide DNA Microarray Analysis of *Francisella tularensis* Strains Demonstrates Extensive Genetic Conservation within the Species but Identifies Regions that are Unique to the Highly Virulent *F. tularensis* subsp. tularensis," Journal of Clinical Microbiology, 2003, 41(7):2924-2931.

Buchele et al., "Studies on pathogenesis and immunity in tularemia II. Immune Response of the white rat to bacterium tularense," Journal of Immunology, 1949, 63(2):135-145.

Burke, "Immunization Against Tularemia Analysis of the Effectiveness of Live *Francisella tularensis* Vaccine in Prevention of Laboratory Acquired Tularemia," Journal of Infectious Diseases, 1977, 135(1):55-60.

Burrows et al., "Molecular characterization of the *Pseudomonas aeruginosa* serotype 05 (PA01) B-band lipopolysaccharide gene cluster," Molecular Microbiology, 1996, 22(3):481-495.

Candela et al., "Poly-gamma-glutamate in bacteria," Molecular Microbiology, 2006, 60(5):1091-1098.

Carlsson et al., "Enzyme-Linked Immunosorben Assay for Immunological Diagnosis of Human Tularemia," Eur. J. Biochem, 2002, 269:6112-6118 pgs.

Casetti et al., "Drug-Induced Expansion and Differentation of Vy9Vo2 T Cells in Vivo: The role of exogenous IL-2," Journal of Immunology, 2005, 1593-1599.

Chain et al., "Complete genome sequence of *Francisella tularensis* LVS (Live Vaccine Strain)," NCBI Reference Sequence: NC_007880.1, Jan. 25, 2012.

Chamberlain, "Evaluation of Live Tularemia Vaccine Prepared in a Chemically Defined Medium," Applied Microbiology, 1965, 13(2):232-235.

Champion et al., "Comparative genomic characterisation of *Francisella tularensis* starains," pLoS Pathogens, 2009, 5:e1000459.

(56) References Cited

OTHER PUBLICATIONS

Chart, "Lipopolysaccharide: Isolation and Characterization," In: Raton B, Arbor A (eds.) Methods in Practical Laboratory Bacteriology, CRC Press, London, Tokyo, 1994, 11-20.

Chen et al., "Tularemia in BALB/c and C57BU6 mice vaccinated with *Francisella tularensis* LVS and challenged intradermally, or by aerosol with virulent isolates of pathogen: protection varies depending on pathogen virulence, route of exposure, host genetic background," Vaccine, 2003, 21:3690-3700.

Chernos et al., "Insertion mutants of the vaccinia virus. The effect of inactivating E7R and D8L genes on the biological properties of the virus. Abstract Only," Mol. Gen. Mikrobiol Virusol., 1993, 2:30-34.

Chertov et al., "Amino acid sequence determination of vaccinia virus immunodominant protein p35 and identification of the gene," Biomed. Science, 1991, 2:151-154.

Chung et al., "A27L Protein Mediates Vaccinia Virus Interaction with Cell Surface Heparan Sulfate," J. Virol., 1998, 72(2):1577-1585.

Clemens et al., "Virulent and Avirulent Strains of *Francisella tularensis* Prevent Acidifcation and Maturation of Their Phagosomes and Escape Into the Cytoplasm in Human Macrophages," Infection and Immunity, 2004, 72(6):3204-3217.

Conlan et al., "Different host defences are required to protect mice from primary systemis vs pulmonary infection with the faculative intracellular bacterial pathogen, *Francisella tularensis* LVS," Microb. Pathog., 2002, 32:127-134.

Conlan, "Vaccines against *Francisella tularensis*—past, present and future," Expert Rev. Vaccines, 2004, 3(3):307-314.

Cooper et al., "CPG 7909, an immunostimulatory TLR9 agonist oligodeoxynucleotide, as adjuvant to Engerix-B HBV Vaccine in healthy adults: A double-blind phase I/II study," Journal of Clinical Immunology, 2004, 24(6):693-701.

Cooper et al., "Safety and immunogenicity of CPG 7909 injection as an adjuvant to Fluarix influenza vaccine," Vaccine, 2004, vol. 22, 3136-3143.

Cowley et al., "Isolation and characterization of *Francisella novicida* mutants defective in lipopolysaccharide biosynthesis," FEMS Microbiol Lett., 2000, 182:63-67.

Dalsgaard, "Saponin Adjuvants," 1974, 243-254.

DATABASE KEGG [Online], "Glutamate metabolism-*Francisella tularensis* subsp. tularensis SCHU S4," XP002468730, Retrieved from http://www.genome.jp/KEGG/Pathway/FTU/FTU00251.HTML, Feb. 19, 2007.

Davis et al., "Pathology of Experimental Pneumonic Plague Produced by Fraction-1 Positive and Fraction-1 Negative Yersinia pestis in Agrican Green Monkeys (*Cercopithecus aethiops*)," Arch. Pathol. Lab. Med, 1996, 120(2):156-163.

Demkowicz et al., "Identification and characterization of vaccinia virus genes encoding proteins that are highly antigenic in animals and are immunodominant in vaccinated humans," Journal of Virology, 1992, 66(1):386-398.

Deng et al., "Identification of *Francisella tularensis* genes affected by iron limitation" Infect. Immun., 2006, 74:4224-4236.

Deng et al., "Site-directed mutagenesis of virtually any plasmid by eliminating a unique slte," Anal. Biochem., 1992, 200:81-88.

Drabick et al., "Analysis of Active Live Immunization Versus Passive Humoral Immunotherapy Against Attenuated and Virulent Strains of *Francisella tularensis*," Vaccine Research, 1997, 6(2):67-74.

Drabick et al., "Passive Protection of Mice against Lethal *Francisella tularensis* (Live Tularemia Vaccine Strain) Infection by the sera of human recipients of the Live Tularemia Vaccine," The American Journal of the Medical Sciences, 1994, 308:83-87.

Dreisbach et al., "Purified Lipopolysaccharide from *Francisella tularensis* Live Vaccine Strain (LVS) Induces Protective Immunity against LVS Infection That Requires B Cells and Gamma Interferon," Infection and Immunity, 2000, 68:1988-1996.

Duncan et al., "Identification and characterization of an extracellular envelope glycoprotein affecting vaccinia virus egress," Journal of Virology, 1992, 66(3):1610-1621.

Dunstan et al., "Comparison of the Abilities of Different Attenuated *Salmonella typhimurium* Strains to Elicit Humoral Immune Responses against a Heterologous Antigen," Infection and Immunity, 1998, 66(2):732-740.

Eigelsbach et al., "Murine Model for Study of Cell-Mediated Immunity: Protection Against Death from Fully Virulent *Francisella tularensis* Infection," Infection & Immunity, 1975, 12(5):999-1005.

Eigelsbach et al., "Prophylactic effectiveness of live and killed tularemia vaccines, I.production of vaccine and evaluation in the white mouse and guinea pig," Journal of Immunology, 1961, 87:415-425.

Elkins et al., "Bacterial DNA Containing CpG Motifs Stimulates Lymphocyte-Dependent Protection of Mice Against Lethal Infection with Intracellular Bacteria," Journal of Immunology, 1961, pp. 2291-2298.

Ellis et al., "Tularemia," Clinical Microbiology Reviews, 2002, 15(4):631-646.

EMBL-Bank Sequence Database, Accession No. AF140738, Jan. 19, 2000.

Engelstad et al., "A Constitutively Expressed Vaccinia GeneEncodes a 42-kDa Glycoprotein Related to Complement Control Factors that Forms Part of the Extracellular Virus Envelope," Virology, 1992, 188:801-810.

Eyles et al., "Protection afforded against aerosol challenge by systemic immunisation with inactivated *Francisella tularensis* live vaccine strain (LVS)," Microbial Pathogenesis, 2008, 44:164-168.

Florence et al., Formulation in vol. 5 of Comprehensive Medicinal Chemistry, Corwin Hansch; Chairman of Editorial Board, Pergamon Press, 1990, 567-591.

Forest et al., "Type IV pili structure, assembly adn immunodominance: applications to vaccine design," Vaccines, 1997, 97:167-173.

Forslund et al., "Direct repeat-mediated deletion of a type IV pilin gene results in major virulence attenuation of *Francisella tularensis*," Molecular Microbiology, 2006, 59(6):1818-1830.

Forslund et al., "Type IV Pili is Required for Virulence of *Francisella tularensis*," Abstract, American Society of Microbiology Biodefense Research meeting, Mar. 20-23, 2005, 2005.

Franke et al., "Use of a Cell-Free System to Identify the Vaccinia Virus L1R Gene Product as the Major Late Myristylated Virion Protein M25," Journal of Virology, 1990, 64(12):5988-5996.

Fulop et al., "Production and Characterization of Monoclonal Antibodies Directed against the Lipopolysaccharide of *Francisella tularensis*," Journal of Clinical Microbiology, 1991, 29:1407-1412.

Fulop et al., "Role of antibody to lipopolysaccharide in protection against low- and high high virulence," Vaccine, 2001, 19:4465-4472.

Fulop et al., "Role of lipopolysaccharide and a major outer membrane protein from *Francisella tularensis* in the induction of immunity against tularaemia," Vaccine, 1995, 13(13):1220-1225.

Fulop et al., "Role of two outer membrane antigens in the induction of protective immunity against *Francisella tularensis* strains of different virulence," FEMS Immunology and Medical Microbiology, 1996, 13:245-247.

GB 0518203.5, Search report, Feb. 27, 2006.

GB 0519161.4, Search Report, Mar. 1, 2006.

Search Report in International Application No. PCT/GB2003/002338, Nov. 3, 2003.

Gil et al., "Presence of Pili on the Surface of *Francisella tularensis*," Infection and Immunity, 2004, 3042-3047.

Golovliov et al., "A method for allelic replacement in *Francisella tularensis*," FEMS Microbiology Letters, 2003, 222:273-280.

Golovliov et al., "Adjuvanticity of ISCOMs incorporating a T cell-reactive lipoprotein of the facultative intracelluar pathogen *Francisella tularensis*," Vaccine, 1995, 13(3):261-267.

Golovliov et al., "Indentification of proteins of *Francisella tularensis* induced during growth in macrophages and cloning of the gene encoding a prominently induced 23-kilodalton protein," Infect. Immun. 65(6):2183-2189, 1997.

Gossman et al., "Quantitative Structure-Activity Relations of γδT Cell Activation by Phosphoantigens," Journal of Med. Chem., 2002, 45:4868-4874.

(56) References Cited

OTHER PUBLICATIONS

Gramzinski et al., "Interleukin 12- and Gamma Interferon-Dependent Protection Against Malaria Conferred by CpG Oligodeoxynucleotide in Mice," Infect. Immun., 2001, 69(3):1643-1649.
Gray et al., "The identification of five genetic loci of *Francisella novicida* associated with intracellular growth," FEMS Microbiology Letters, 2002, 215:53-56.
Green et al., "Efficacy of the live attenuated *Francisella tularensis* vaccine (LVS) in a murine model of disease," Vaccine, 2005, 23:2680-2686.
Greenspan et al., "Defining Epitopes: Its not as easy as it seems," Nature Biotechnology, 1999, 17:936-937.
Groisman, "How bacteria resist killing by host—defense peptides," Trends Microbiol, 1994, 2:444-449.
Hahn et al., "The type-4 pilus is the major virulence-associated adhesin of *Pseudomonas aeruginosa* —a review," Gene, 1997, 99-108.
Hartley et al., "Grey variants of the line vaccine strain of *Francisella tularensis* lack lipopolysaccharide O-antigen, show reduced ability to survive in macrophages and do not induce protective immunity in mice," Vaccine, 24:989-996, 2006.
Hartmann et al., "Delineation of a CpG Phosphorothioate Oligodeoxynucleotide for Activating Primate Immune Responses in Vitro and In Vivo," Immunology, 2000, 164:1617-1624.
Hatch et al., "Immunogenic Substances in culture filtrates and lysates of *Pasteurella tularensis*," Journal of Bacteriology, Sep. 1964, 88(3):566-573.
Henderson et al., "The Looming Threat of Bioterrorism," Science, 1999, 283:1279-1282.
Heraud et al., "Protection from lethal monkeypox challenge afforded by a four-gene-combination DNA vaccine followed by boosting with CpG-adjuvanted monkeypox proteins plus CpG Abstract Only," Journal of Medical Primatology, 2006, 35:4-5.
Hertle et al., "Dual-function vaccine for *Pseudomonas aeruginosa*: characterization of a chimeric exotoxin A-pilin protein," Infection and Immunity, 2001, 69(11):6962-6969.
Hollis et al., "*Francisella philomiragia* comb. Nov. (Formerly *Yersinia philomiragia* ) and *Francisella tularensis* Biogroup Novicida(Formerly *Francisella novicida* ) Associated with Human Disease," Journal of Clinical Microbiology, 1989, 27(7):1601-1608.
Hooper et al., "DNA vaccination with Vaccinia Virus L1R and A33R Genes Protects Mice against a Lethal Poxvirus Challenge," Virology, 2000, 266:329-339.
Hooper et al., "Four-gene-combination DNA vaccine protects mice against a lethal vaccinia virus challenge and elicits appropriate antibody responses in nonhuman primates," Virology, 2003, 306:181-195.
Hsiao et al., "Vaccinia VirusEnvelope D8L Protein Binds to Cell Surface Chondroitin Sulfate and Mediates the Absorption of Intracellular Mature Virions to Cells," Journal of Virology, 1999, 73(10):8750-8761.
Hubalek et al., "Comparative proteome analysis of cellular proteins extracted from highly virulent *Francisella tularensis* ssp. tularensis and less virulent *F. tularensis* ssp. holarctica and *F. tularensis* ssp. mediaasiatica," Proteomics, 2004, 4:3048-3060.
Huseby et al., "Practical points regarding routine determination of γ-glutamyl transferase (γ-GT) in serum with a kinetic method at 37° C.,," Scandinavian Journal Clin. Lab. Invest., 34:357-363, 1974.
Isherwood et al., "Vaccination strategies for *Francisella tularensis*," Advanced Drug Delivery Reviews, 2005, 57(9):1403-1414.
Itamura et al., "Biological and immunological characterization of influenza virus haemagglutinin expressed from the haemagglutinin locus of vaccinia virus," J. Gen. Virology, 1990, 71:1293-1301.
Johansson et al., "Worldwide Genetic Relationships among *Francisella tularensis* Isolates Determined by Multiple-Locus Variable-Number Tandem Repeat Analysis," Journal of Bacteriology, 186(17):5808-5818, 2004.
Johnson et al., "Routes of Administration and Dosage Regimes," Comprehensive Medicinal Chemistry, 1990, 5:593-613.

Kadzhaev et al., "Identification of Genes Contributing to the Virulence of *Francisella tularensis* SCHU S4 in a Mouse Intradermal Infection Model," PLoS ONE, 2009, vol. 4, Issue 5, e5463; 1-11.
Karlsson et al., "Sequencing of the *Francisella tularensis* Strain Schu 4 Genome Reveals the Shikimate and Purine Metabolic Pathways, Targets for the Construction of a Rationally Attenuated Auxotrophic Vaccine," Microbial & Comparative Genomics, 2000, 5(1):25-39.
Kawula et al., "Use of Transposon-Transposase Complexes to Create Stable Insertion Mutant Strains of *Francisella tularensis* LVS," Applied and Environmental Microbiology, 2004, 70:6901-6904.
Kenne et al., "Bacterial Polysaccharides, The Polysaccharides," Molecular Biology, 1983, vol. 2, pp. 287-362.
Khlebnikov et al., "Outer Membrane of a lipopolysaccharide-protein complex (LPS-17 KdA Protein) as chemical tularemia vaccines," FEMS Immunology and Medical Microbiology, 1996, 13:227-33.
Kieffer et al., "*Francisella novicida* LPS has greater immunobiological activity in mice than *F. tularensis* LPS, and contributes to *F. novicida* murine pathogenesis," Microbes and Infection, 2003, 5:397-403.
Kiss et al., "Characterization of fig operon mutants of *Francisella novicida* U112," FEMS Micriobiol Letters, 2008, 285:270-277.
Klinman et al., "CpG Motifs Present in Bacterial DNA Rapidly Induce Lymphocytes to Secrete Interleukin 6, Interleukin 12, and Interferon γ," Proc. Natl. Acad. Sci. USA, Apr. 1996, 93:2879-2883.
Klinman et al., "Immune Recognition of Foreign DNA: A Cure for Bioterrorism?," Immunity, 1999, 11:123-129.
Klinman et al., "Immunotherapeutic Uses of CpG Oligodeoxynucleotides," Nature Reviews/Immunology, 2004, 4:249.
Knirel et al., "Somatic antigens of *Pseudomonas aeruginosa*," Eur. J. Biochem., 1985, 150:541-550.
Koskela et al., "Cell-mediated immunity against *Francisella tularensis* after natural infection," Scandinavian Journal of Infectious Diseases, 1980, 12(4):281-287.
Krieg et al., "Brief Communication, Oligodeoxynucleotide Modifications Determine the Magnitude of B Cell Stimulation by CpG Motifs," Antisense and Nucl. Acid Drug Dev., 1996, 6:133-139.
Krieg et al., "CpG motifs in bacterial DNA trigger direct B-cell activation," Nature, 1995, 374:546-549.
Krieg, "Leukocyte Stimulation by Oligodeoxynucleotides," Applied Antisense Oligonucleotide Technology, C.A., Stein and Krieg (Eds), John Wiley and Sons, Inc., NY , 1998, Ch. 24, pp. 431-448.
Krieg, "The CpG motif: Implications for clinical immunology," Abstract OnlyBioDrugs, 1998, 10(5):341-346.
Kuolee et al., "Vaccines and therapeutic agents for tularemia," Informa Healthcare, 2007, 267-275.
Kus et al., "Significant differences in type IV pilin allele distribution among *Pseudomonas aeruginosa* isolates from cystic fibrosis (CF) versus non-CF patients," Microbiology, 2004, 150:1315-1326.
Laemmli "Cleavage of structural Proteins during the Assembly of the Head of Bacteriophage T4," Nature, 1970, 227, pp. 680-685.
Lai et al., "Expression of IgIC is necessary for intracellular growth and induction of apoptosis in murine macrophages by *Francisella tularensis*," Microbial Pathogenesis, 2004, 37:225-230.
Larsson et al., "Molecular evolutionary consequences of niche restriction in *Francisella tularensis*," PLoS Pathoges, 2009, 5:e1000472.
Larsson et al., "The complete genome sequence of *Francisella tularensis*, the causative agent of tularemia," Nature Genetics, 2005, 37(2):153-159.
Lascola et al., "Rapid comparative genomic analysis for clinical microbiology," Genome Res, 2008, 18:742-750.
Lauriano et al., "MgIA regulates transcription of virulence factors necessary for *Francisella tularensis* intraamoebae and intramacrophage survival," Proc. Natl. Acad. Sci. USA, 2004, 101:4246-4249.
Lavine et al., "Immunization with heat-killed *Francisella tularensis* LVS elicits protective antibody-mediated immunity," Eur. J . Immunology, 2007, 37:3007-3020.
Law et al., "Antibody Neutralization of the Extracellular Enveloped Form of Vaccinia Virus," Virology, 2001, 280:132-142.

(56) References Cited

OTHER PUBLICATIONS

Lefeber et al., "Th1-Directing Adjuvants Increase the Immunogenicity of Oligosaccharide-Protein Conjugate Vaccines Related to *Streptococcus pneumoniae* Type 3," Infection and Immunity, 2003, 6915-6920.

Lipman et al., "Rapid and Sensitive Protein Similiarity Searches," Science, 1985, 227:1435-1441.

Mack et al., "A new cell Assay to Determine the Virulence of *Francisella tularensis*," Letters in Applied Microbiology, 1994, 19:158-160.

Maier et el., "In Vivo Himarl1-Based Transposon Mutagenesis of *Francisella tularensis*," Applied Environmental Microbiology, 2006, 72(3):1878-1885.

Mann et al., "Rationally designed tularemia vaccines," Expert Rev. Vaccines, 2009, 8(7):877-885.

McCrumb et al., "Aerosol Infection of Man with *Pasteurella tularensis*," Bacteriol Rev., 25(3):262-7, 1961.

McIntosh et al., "Vaccinia Virus Glycoprotein A34R is Required for Infectivity of Extracellular Enveloped Virus," Journal of Virology, 1996, 70(1):272-281.

McLendon et al., "*Francisella tularensis*: Taxonomy, Genetics, and Immunopathogenesis of a Potential Agent of Biowarfare," Annual Rev. Microbiology, 2006, 60:167-185.

McMurry et al., "Diversity of *Francisella tularenis* Schu4 antigens recognized by T lymphocytes after natural infections in humans: identification of candidate epitopes for inclusion in a rationally designed tularemia vaccine," Vaccine, 2007, 25(16):3179-91.

Michell et al., "A capB mutant of *Francisella tularensis*," URL:http://www.sgm.ac.uk/meetings/pdfabstracts/keele2005abs.pdf (2008), Sep. 12, 2005.

Michell et al., Unpublished U.S. Appl. No. 10/550,773, filed Jul. 20, 2006.

Mitchell et al., "Development of real-time PCR assays for the specific detection of *Francisella tularensis* ssp. *Tularensis*, holartica and mediaasiaatica," Molecular and Cellular Probes, 2010, 24:72-76.

Nano et al., "A *Francisella tularensis* Pathogenicity Island Required for Intramacrophage Growtn," Journal of Bacteriology, 2004, 186(19):6430-6436.

Narayanan et al., "Immunotherapy of Tularemia: Characterisation of a monoclonal antibody reactive with *Francisella tularensis*," Journal of Leukocyte Biology, 1993, 53:112-116.

Nielsen et al., "Peptide nucleic acids (PNAs): Potential anti-sense and anti-gene agents," Anti-Cancer Drug Des., 1993, 8:53-63.

Nutter et al., "Antigens of *Pasteurella tularensis*: Preparative Procedures," Applied Microbiology, Jul. 1971, 22(1):44-48.

O'Hagan, "Recent developments in vaccine delivery systems," Current Drug Targets, Infectious Disorders, Bentham Science Publishers, Hilversum, NL, 2001, 1(3):273-286.

Olsufiev et al., "Comparative study of strains of *B. tularense* in the old and new world and their taxonomy," J. Hyg. Epidemiol. Microbiol. Immunol., 1959, 3:138-149.

Ormsbee et al., "Studies on Bacterium Tularense Antigens I. The Isolation, Purification and Biologic Activity of Antigen Preparations from Bacterium tularense," Journal of Immunology, 1954, 74:351-358.

Ormsbee et al., "Studies on Bacterium Tularense Antigens, I. Chemical and Physical Characteristics of Protective Antigen Preparations," Journal of Immunology, 1954, 74(5):359-370.

Overholt et al., "An analysis of forty-two cases of laboratory-acquired tularemia. Treatment with broad spectrum antibiotics," The American Journal of Medicine, 1961, 30:785-806.

Oyston et al., "Tularaemia vaccine: past, present and future," Antonie van Leeuwenhoek, 2005, 87:277-281.

Pammit et al., "Intranasal vaccination with a defined attenuated *Francisella novicida* strain induces gamma interferon-dependent antibody-mediated protection against tularemia," Infect. Immun., Apr. 2006, 74(2):2063-2071.

Parkinson et al., "Vaccinia Virus Gene A36R Encodes a Mr 43-50 K Protein on the Surface of Extracellular Enveloped Virus," Virology, 1994, 204(1):376-390.

Pavlov et al., "Cryptic plasmid pFNL10 from *Francisella novicida*-like F6168: the base of plasmid vectors for *Francisella tularensis*," FEMS Immunol. Med. Microbiol., 1996, 13:253-256.

Pechous et al., "A *Francisella tularensis* Schu S4 Purine Auxotroph is Highly Attenuated in Mice but Offers Limited Protection Against Homologous Intranasal Challenge," PLoS ONE, 2008, 3(6):1-10.

Pechous et al., "Construction and Characterization of an Attenuated Purine Auxotroph in a *Francisella tularensis* Live Vaccine Strain," Infection and Immunity, 2006, 74(8):4452-4461.

Petrosino et al., "Chromosome rearrangement and diversification of *Francisella tularensis* revealed by the type B (OSU18) genome sequence," J. Bacteriol, 2006, 188(19):6977-85.

Petrovsky et al., "Freeing vaccine adjuvants from dangerous immunological dogma," Expert Rev. Vaccines, 2008, 7(1):7-10.

Petrovsky et al., "New-Age Vaccine Adjuvants: Friend or Foe?," BioPharmInternational.com., Aug. 2, 2007, 12 pgs.

Phelps et al., "Evaluating the Use of PcG DNA as an Antiviral Therapy," Antiviral Research, 2006, 70(1):A74 XP009078434 Abstract.

Poquet et al., "Expansion of Vy9Vo2 T Cells Is Triggererd by *Francisella tularensis* -Derived Phosphoantigens in Tularemia but Not after Tularemia Vaccination," Infection and Immunity, 1998, 66(5):2107-2114.

Prior et al., "Preliminary analysis an annotation of the partial genome sequence of *Francisella tularensis* strain Schu 4," Journal of Applied Microbiology, 2001, 91:614-620.

Pulford et al., "Differential efficacy of vaccinia virus envelope proteins administered by DNA immunisation in protection of BALB/c mice from a lethal intranasal poxvirus challenge,"Vaccine, 2004, 22:3358-3366.

Qin et al., "Identification of an essential *Francisella tularensis* subsp. tularensis virulence factor," Infection and Immunity, 2009, 152-161.

Qin et al., "Identification of transposon insertion mutants of *Francisella tularensis* tularensis strain Schu S4 deficient in intracellular replication in the hepatic cell line HepG2," BMC Microbiology, 2006, 6:69.

Quarry et al., "A *Francisella tularensis* subspecies novicida purF mutant, but not a purA mutant, induces protective immunity to tularemia in mice," Vaccine, 2007, 25:2011-2018.

Reed et al., "A Simple Method of Estimating Fifty Per Cent Endpoints," Am. J. Hygiene, 1938, 27(3):493-497.

Rees et al., "CpG-DNA protects against a lethal orthopoxvirus infection in a murine model," Antiviral Research, 2005, 65:87-95.

Richards et al., "Identification of *Francisella* genes up-regulated in the macrophage," Poster at the International Conference on *Tularemia*, Nov. 2006, 7 pages.

Robertson et al., "Detection of the Osmoregulator Betaine in Methanogens," Applied and Environmental Microbiology, 1990, 56:1504-1508.

Robertson et al., "β-Aminoglutaric acid is a major soluble component of *Methanococcus thermolithotrophicus*," Biochimica et Biophysica Acta, 1989, 992:320-326.

Rodriquez et al., "Inducible Gene Expression from Vaccinia Virus Vectors," Virology, 1990, 177:239-250.

Rohmer et al., "Comparison of *Francisella tularensis* genomes reveals evolutionary events," Genome Biol, 2007, 8:R102.

Rohmer et al., "Potential source of *Francisella tularensis* live vaccine strain attenuation determined by genome comparison," Infectious Immunology, 2006, 74(12):6895-6906.

Roper et al., "Extracellular Vaccine Virus Envelope Glycoprotein Encoded by the A33R Gene," Journal of Virology, 1996, 70(6):3753-3762.

Russell et al., "The efficacy of ciprofloxacin and doxycycline against experimental ularaemia," J. Antimicrob. Chemother., 1998, 41:461-5.

Salmons et al., "Vaccinia Virus Membrane Proteins p8 and p16 are Cotranslationally Inserted into the Rough Endoplasmic Reticulum and Retained in the Intermediate Compartment," Journal of Virology, 1997, 71(10):7404-7420.

Salomonsson et al., "A Role for a Type IV Pilus in Virulence of *Francisella tularensis*," Abstract, Society of General Microbiology, 155th Meeting, Sep. 6-9, 2004, Trinity College, Dublin, Ireland, 2004.

(56) References Cited

OTHER PUBLICATIONS

Salomonsson et al., "Role for a Type IV Pilus Virulence of *Francisella tularensis*," Abstract, American Society for Microbiology Meeting, Jun. 5-9, 2005, May 2005.
Salyers et al., "Vaccines and Other Approaches to Modulating the Immune Response," Bacterial Pathogenesis a Molecular Approach, 1994, p. 90.
Sambrook et al., "Molecular Cloning," Molecular Cloning: A laboratory Manual, 2001, 3rd ed., Spring Harbor laboratory New York, NY, 2001, pp. v-xx.
Samrakandi et al., "Genome diversity among regional populations of *Francisella tularensis* subspecies," FEMS Microbiology Letters, 2004, 237:9-17.
Sandstrom et al., "A Capsule-Deficient Mutant of *Francisella tularensis* LVS Exhibits Enhanced Sensitivity to Killing by Serum but Dimished Sensitivity to Killing by Polymorphonuclear Leukocytes," Infection and Immunity, 1988, 56(5):1194-1202.
Sandstrom et al., "Antigen from Francisella tularensis: Nonidentity Between Determinants Participating in Cell-Mediated and Humoral Reactions," Infect. Immun., 1984, 12(1):101-106.
Sandstrom, "The Tularaemia Vaccine," J. Chem. Tech. Biotechnology, 1994, 59:315-320.
Sanger et al., "DNA sequencing with chain-terminating inhibitors," Proc. Natl. Acad. Sci. USA, 1977, 74:5463-5467.
Shen et al., "Mice sublethally infected with *Francisella novicida* U112 develop only marginal protective immunity against systemic or aerosol challenge with virulent type A or B strains of *F. tularensis*," Microbial Pathogenesis, 2004, 37:107-110.
Simon et al., "A broad host range mobilisation system for in vitro genetic engineering: transposon mutagenesis in Gram-negative bacteria," Biotechnology, 1:784-791, 1983.
Sonnhammer et al., "A hidden Markov model for predicting transmembrane helicesinprotein sequences," In: Glasgow S, Littlejohn T et al. (eds.), 1998, 175-182.
Sorokin et al., "*Francisella tularensis* resistance to bactericidal action of normal human serum," FEMS Immunology and Medical Microbiology, 1996, 13:249-252.
Su et al., "Genome-Wide Identification of *Francisella tularensis* Virulence Determinants," Infection and Immunity, 2007, 3089-3101.
Sullivan et al., "Characterization of the Siderophore of *Francisella tularensis* and Role of fslA in Siderophore production," Journal of Bacteriology, 2006, 188:3785-3795.
Svensson et al., "Evolution of Subspecies of *Francisella Tularensist*," Journal of Bacteriology, Jun. 2005, 187, 3903-3908.
Szoka, "Comparative Properties and Methods of Preparation of Lipid Vesicles (Liposomes)," Ann. Rev. Biophy. Bioeng., 9:467-508, 1980, 467-508.
Tarnvik et al., "Nature of Protective Immunity to *Francisella tularensis*," Review of Infectious Diseases, 1989, 11(3):440-451.
Tarnvik et al., "Orchestration of the protective immune response to intracellular bacteria: Francisella," FEMS Immunology and Medical Microbiology, 1996, 13(3):221-225.
Tarnvik et al., "Stimulation of Human Lymphocytes by a Vaccine Strain of *Francisella tularensis*," Infection and Immunity, 1975, 12(5):951-957.
Tarnvik et al., "Stimulation of Subpopulations of Human Lymphocytes by a Vaccine Strain of *Francisella*," Infection and Immunity, 1978, 20(3):698-704.
Tempel et al., "Attenuated *Francisella novicida* Transposon Mutants Protect Mice against Wild-Type Challenge," Infection and Immunity, 2006, 74(9):5095-5105.
Tigertt, "Soviet viable Pasteurella tularensis vaccines," Bacteriol. Rev. 26:354-373, 1962.
Titball et al., "Will the enigma of *Francisella tularensis* virulence soon be resolved?," Trends in Microbiology, 2003, 11(3):118-123.
Tonjum et al., "The pilus colonization factor of pathogenic neisserial species: organelle biogenesis and structure/function relationships—a review," Gene, 1997, 155-163.
Twine et al., "A Mutant of *Francisella tularensis* Strain SCHU S4 Lacking the Ability to Express a 58-Kilodalton Protein Is Attenuated for Virulence and Is an Effective Live Vaccine," Infection and Immunity, 2005, 73(12):8345-8352.
Vanderplasschen et al., "Intracellular and extracellular vaccinia virions enter cells by different mechanisms," Journal of Gen. Virology, 1998, 79:877-887.
Vinogradov et al., "Structural Analysis of *Francisella tularensis* Lipopolysaccharide," Eur. J. Biochem., 2002, 269:6112-6118.
Vogel et al., "Acetylornithinaase of *Escherichia coli*: Partial Purification and some Properties," J. Biol. Chem., 1955, 218:97-106.
Waag et al., "Cell-Mediated and humoral immune responses after vaccination of human volunteers with the live vaccine strain of *Francisella tularensis*," Clin. Diagn. Lab. Immunol, 1995, 2:143-148.
Waag et al., "Immunogenicity of a new lot of *Francisella tularensis* live vaccine strain in human volunteers," FEMS Immunol. Med. Microbiol., 1996, 13:205-209.
Waldo et al., "Proteome Cataloging and relative quantification of *Francisella tularensis* strain Schu4 in 2D PAGE using preparative isoelectric focusing," Journal of Proteome Research, 2007, 6(9):3484-3490.
Weiner, "The immunobiology and clinical potential of immunostimulatory CpG oligodeoxynucleotides," Journal of Leukocyte Biology, 2000, 68:456-463.
Westphal et al., "Bacterial Lipopolysaccharides," Methods in Carbohydrate Chemistry, Ed. Roy L. Whistler, Academic Press, 1965, 5:83-91.
Whitfield et al., "Modulation of the surface architecture of gram-negative bacteria by the action of surface polymer:Lipid A-core ligas and by determinants of polymer chain length," Mol. Micro., 1997, 23(4):629-638.
Williamson et al., "A sub-unit vaccine elicits IgG in serum, spleen cell cultures and bronchial washings and protects immunized animals against pneumonic plague," Vaccine, 1997, 15:1079-1084.
Xiao et al., "A protein-based smallpox vaccine protects mice from vaccinia and ectromelia virus challenges when given as a prime and single boost," Vaccine, 2007, 25:1214-1224.
Yamamoto et al., "Ability of oligonucleotides with certain palindromes to induce interferon production and augment natural killer cell activity is associated with their base length, Abstract Only," Antisense Research and Development, 1994, 4:119-122.
Zhao et al., "Effect of different chemically modified oligodeoxynucleotides on immune stimulation," Abstract Only, Biochemical Pharmacology, 1996, 51:173-182.
Reyrat et al., Counterselectable Markers: Untapped Tools for Bacterial Genetics and Pathogenesis, Infection and Immunity, Sep. 1998, pp. 4011-4017.

* cited by examiner

Fig.2.

GGT activity of *F. tularensis* Δ*ggt* (▨) and *F. tularensis* SCHU S4 (☐), measured as the $A_{405}$ of p-nitroanilide released from L→-glutamyl-p-nitroanilide by each strain.

Fig.3.

Growth of *F. tularensis* Δ*ggt* (▨) and *F. tularensis* SCHU S4 (☐) in CDM with and without free cysteine, and without free cysteine but supplemented with GSH (0.6 mM or 1.3 mM).

Fig.4.

Recovery of viable F. tularensis Δggt (▨) compared to F. tularensis SCHU S4 (☐) from J774A.I cells inoculated with a MOI of ten bacteria per macrophage. This experiment was repeated in triplicate, the data displayed here being taken from one representative experiment.

Fig.5.

Survival of Balb/C mice administered with F. tularensis Δggt (8.75 CFU [◇], 8.75 CFU [■], 87.5 x $10^2$ CFU [∗], 8.75 x $10^3$ CFU [×], 8.75 x $10^4$ CFU [♦], 8.75 x $10^5$ CFU [ | ], 8.75 x $10^6$ CFU [▲]) compared to mice administered with 1.3 x $10^3$ CFU F. tularensis SCHU S4 (o). The MLD of F. tularensis Δggt was calculated as ~2 x $10^6$ CFU, compared to a wild type F. tularensis MLD of ~1 CFU.

Fig.6.

Survival of mice vaccinated with *F. tularensis* Δ*ggt* (8.75 CFU [◇], 87.5 CFU [■], 8.75 x $10^2$ CFU [▲], 8.75 x $10^3$ CFU [×], 8.75 x $10^4$ CFU [*], 8.75 x $10^5$ CFU [◆], or 8.75 x $10^6$ CFU [|]) and naïve mice (○) challenged with 100 MLD of *F. tularensis* SCHU S4.

GAMMA-GLUTAMYL TRANSPEPTIDASE ATTENUATED *FRANCISELLA*

CROSS REFERENCE TO RELATED APPLICATIONS

This application is the U.S. national phase of International Application No. PCT/GB2010/000743 filed on Apr. 14, 2011, and published in English on Oct. 21, 2010, as International Publication No. WO 2010/119245 A2, which application claims priority to Great Britain Patent Application No. 0906234.0 filed on Apr. 14, 2009, the contents of both of which are incorporated herein by reference.

The present disclosure relates to a mutated *Francisella* bacterium, pharmaceutical compositions comprising the same, in particular vaccine compositions, and use of the bacterium and compositions for treatment and/or prophylaxis, in particular the treatment or prophylaxis of tularemia.

Tularemia (also known as "rabbit fever", "deer-fly fever") is a serious infectious disease caused by the bacterium *Francisella tularensis*. A small, gram-negative, non-motile coccobacillus. The bacterium has several subspecies with varying degrees of virulence. The most important of the species is *F. tularensis tularensis* (Type A), which is found in North America and is highly virulent for humans and domestic rabbits. *F. tularensis holarctica* (Type B) occurs mainly in aquatic rodents (beavers, muskrats) in North America and in hares and small rodents in northern Eurasia. It is less virulent in humans and rabbits. The primary vectors are ticks and deer flies, but the disease can also be spread through other arthropods. However, waterborne infection accounts for 5 to 10% of all tularemia in the US.

Currently three subspecies of *Francisella tularensis* have been identified: *tularensis* (sometimes known as *nearctica* or 'type A'), *holarctica* (sometimes known as *palaearctica* or 'type B'), and *mediasiatica* (see FIG. 1). The three subspecies are broadly separated by geographical location and by altered virulence in man. Subspecies *holarctica* can be further divided into three biovars: I, which is erythromycin sensitive; II, which is resistant to erythromycin, and III, isolates from Japan (also known as biovar *japonica*). Subspecies *tularensis* can be further divided into two distinct dales, A.I. and A.II., which are based on variable-number tandem repeat analysis and broadly on geographical location (Johansson et al., 2004).

Disease in previously healthy humans is usually caused by *F. tularensis* subspecies *tularensis* or *F. tularensis* subspecies *holarctica*, with the former being of high virulence and the latter of moderate virulence. Infection with *F. tularensis* subspecies *mediasiatica* only causes mild disease in humans (Hubálek et al., 2004).

A live attenuated vaccine strain of *F. tularensis* subspecies *holarctica* (LVS), also denoted FSC155 has been shown to protect human volunteers against inhalational challenge with ten infectious doses of *F. tularensis* subspecies *tularensis*, although only partial protection was afforded against 100 and 1000 infectious doses (McCrumb, 1961). It is thought that LVS was itself derived from a vaccine strain, known as 'strain 15 restored' (currently denoted FSC338) which was attenuated by continuous in vitro subculture at the Gamaleia Institute in the USSR in the 1930's where it was used to immunise tens of thousands of people living in tularemia endemic areas (Tigertt, 1962). In 1956 vaccine strains including 'strain 15 restored' were transferred from the Gamaleia Institute to the United States Army Medical Research Institute of Infectious Diseases (Tigertt, 1962), where 'strain 15 restored' was subjected to serial animal passage for the isolation of a culture that was ultimately selected for vaccine production in the United States of America and introduced as *F. tularensis* LVS (Eigelsbach and Downs, 1961). LVS was used, under the status of Investigational New Drug, to immunise laboratory workers, with a subsequent reduction of the incidence of laboratory acquired tularemia at the United States Army Medical Research Institute of Infectious Diseases from 5.7 cases per 1000 person years of risk to 0.27 cases per 1000 person years of risk (Burke, 1977). However, it has been reported that some individuals vaccinated with LVS go on to develop tularemia, and also that the immunogenicity of LVS can be variable due to sub-populations of LPS O-antigen-deficient bacteria present in vaccine cultures (Eigelsbach and Downs, 1961; Hartley et al., 2006). The molecular basis of the attenuation of *F. tularensis* LVS remains unclear. The genome sequence of LVS (Chain et al., 2006) has revealed >90% identity to that of the fully virulent *F. tularensis* subspecies *tularensis* strain SCHU S4, although by comparison with that of strain SCHU S4, the genome of LVS appears to have undergone significant rearrangement. One genomic region that is missing in LVS compared to SCHU S4 is associated with the production of type IV pili, which may partly account for the attenuation of the vaccine strain, particularly in light that a *F. tularensis* subspecies *holarctica* pilA strain was also shown to be attenuated (Forslund et al., 2006). However, with the issues of safety, efficacy, and the undefined nature of the vaccine in mind, the US Food and Drug Administration rescinded the Investigational New Drug status of LVS and its use was restricted to high risk groups. Furthermore, its use in post-exposure prophylaxis is not recommended.

Tularemia may be spread by direct contact with contaminated animals or material, by ingestion of poorly cooked flesh of infected animals or contaminated water, or by inhalation (there is one recorded incident of the infection caught through inhalation of pathogen whilst, mowing the lawn). As no vaccine is available to the general public, the best way to prevent tularemia infection is to wear rubber gloves when handling or skinning rodents or lagomorphs (such as rabbits), avoid ingesting uncooked wild game and untreated water sources, and wearing long-sleeved clothes and using an insect repellent to prevent tick and insect bites as tularemia can also be transmitted by biting flies, particularly the deer fly *Chrysops discalis*. Individual flies can remain infective for 14 days and ticks for over two years.

Depending on the site of infection, tularemia has six characteristic clinical syndromes: ulceroglandular (the most common type representing 75% of all forms), glandular, oropharyngeal, pneumonic, oculoglandular, and typhoidal.

The incubation period for tularemia is 1 to 14 days, although most human infections become apparent after 3 to 5 days. Generally the clinical signs include fever, lethargy, anorexia, signs of septicemia, and possibly death. Animals rarely develop the skin lesions seen in people.

Subclinical infections are common and animals often develop specific antibodies to the organism. Fever is moderate or very high and tularemia *bacillus* can be isolated from blood cultures at this stage. Face and eyes redden and become inflamed. Inflammation spreads to the lymph nodes, which enlarge and may suppurate (mimicking bubonic plague). Lymph node involvement is accompanied by a high fever. Death only occurs in less than 1% of cases, if therapy is initiated promptly.

Upon entry into the host, *F. tularensis* is able to evade the immune system and replicate in the cytosol of infected macrophages. *F. tularensis* spreads from the site of infection via the regional lymph nodes and disseminates systemically to organs including the liver, spleen and lungs.

The drug of choice is Streptomycin. Tularemia may also be treated with gentamicin for ten days, tetracycline-class drugs such as doxycycline for 2-3 weeks, chloramphenicol or fluoroquinolones.

Given the debilitating nature of the infection, that no prophylactic treatment/vaccine is available which is suitable for use in the general public and the infection is difficult to treat, an effective prophylactic therapy and/or treatment of the disease would be useful.

In one aspect there is provided an attenuated *Francisella* bacterium, wherein the ggt gene (gamma glutamyl transpeptidase gene) is silenced or deleted.

BRIEF DESCRIPTION OF THE FIGURES

FIG. 2 shows the results of an assay to measure the p-nitroanilide released from Lγ-glutamyl-p-nitroanilide by *F. tularensis* Δggt (■) and *F. tularensis* SCHU S4 (□), as a measure of the GGT enzymatic activity of the strains FIG. 3 shows the growth rates of *F. tularensis* Δggt (■) and *F. tularensis* SCHU S4 (□), under various conditions FIG. 4 shows the amount of *F. tularensis* Δggt (■) and *F. tularensis* SCHU S4 (□) recovered from macrophage cells, an in vitro model to simulate in vivo infection by the bacteria FIG. 5 shows the survival rate of mice administered with one of various doses of *F. tularensis* Δggt or $1.3 \times 10^3$ CFU of *F. tularensis* SCHU S4 (□). The corresponding data for *F. tularensis* Δggt is also shown in Table 2. This figure demonstrates the toxicity/attenuation of the strain in vivo FIG. 6 shows the survival rates of mice vaccinated with various doses of *F. tularensis* Δggt and then challenged with 100× the median lethal dose (MLD) of *F. tularensis* SCHU S4 in comparison to naive mice subjected to the same challenge. The figure shows the ability of attenuated *F. tularensis* Δggt to protect against challenge with the virulent strain. The corresponding data is also shown in Table 3.

Figure 1:
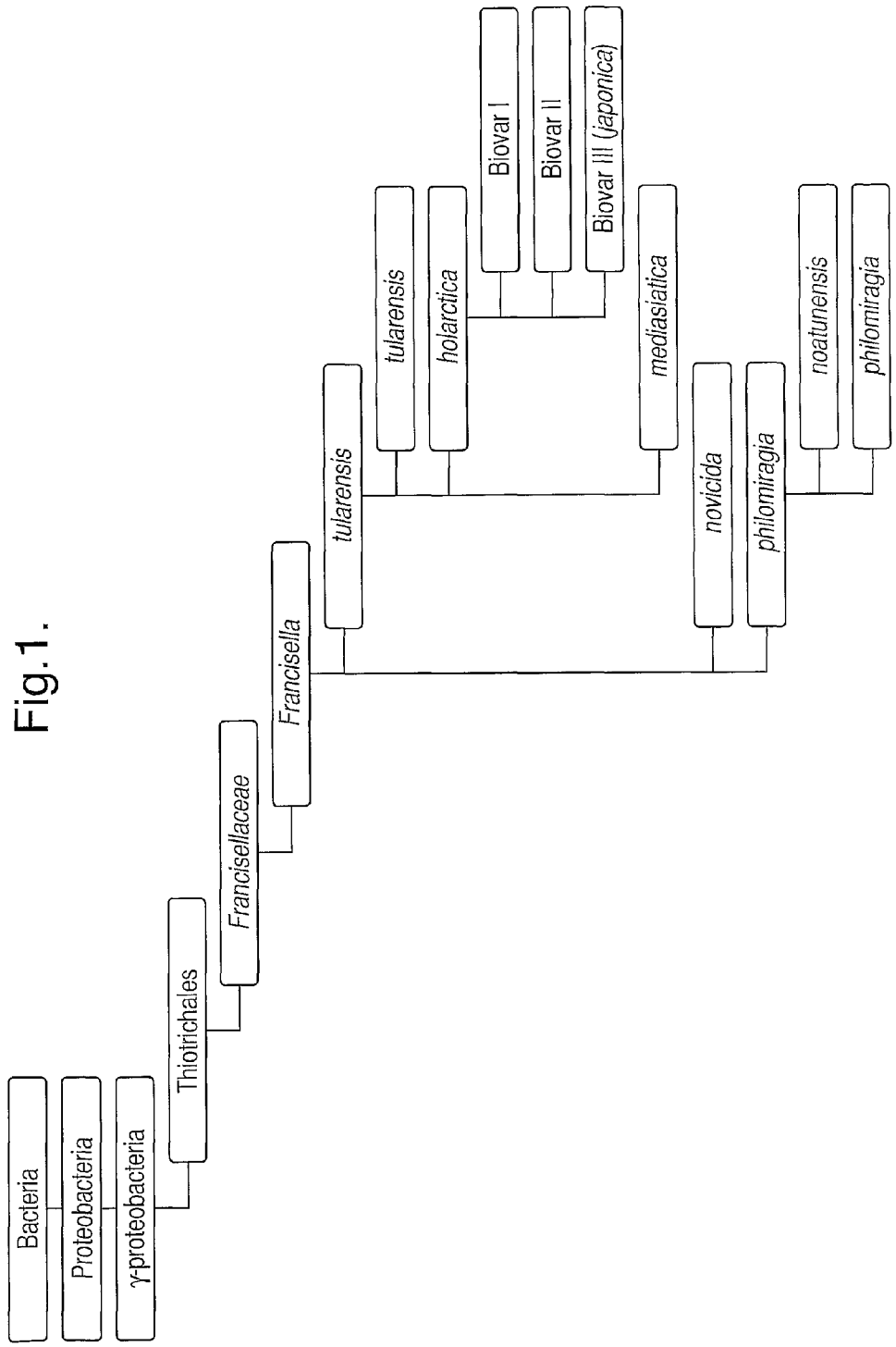
FIG. 1 shows the taxonomy of *Francisella*

The enzyme γ-glutamyl transpeptidase (GGT) catalyses the hydrolysis of γ-glutamyl compounds, mediating the transfer of γ-glutamyl moieties to amino acids and peptides. GGT is reported to have a variety of functions, with one of the major roles being participation in the γ-glutamyl cycle, where it catalyses the degradation of the antioxidant molecule reduced glutathione (GSH) to L-γ-glutamyl and L-cysteinylglycine in the first step of a reaction resulting in the generation of cysteine.

The ggt gene appears to be upregulated when the bacteria are deprived of iron, a condition which is hypothesised to correspond to the conditions the bacteria experience when infecting a host.

Details of the ggt gene can be found at in the NCBI database (Entrez Gene; gene ID 3192241).

The gene ggt as employed herein is intended to refer to gene ID 3192241 or a gene at least 85, 86, 87, 88, 89, 90, 91, 92, 93, 94, 95, 96, 97, 98, 99% identical thereto.

Percentage identity analysis may, for example be performed using software such as BLAST.

It seems that when the ggt gene is deleted or silenced the bacteria become dependent on exogenous sources of cysteine for growth and/or replication. FIG. 3 shows the reduced ability of the ggt deleted (Δ ggt) mutant to grow in the absence of exogenous cysteine. In systems minus cysteine the levels of ggt deleted (Δ ggt) mutant (symbol ■ on the figure) produced are lower, as measured by optical density, than the levels of SCHU S4 (□) produced. The latter does not require exogenous cysteine to grow because it retains the ggt gene. The SCHU S4 strain does however require the presence of exogenous GSH as a source for generating the cysteine. In the system where exogenous GSH and cysteine were provided, the growth of (Δ ggt) and SCHU S4 were approximately equivalent.

FIG. 2 shows the reduced ability of the ggt deleted (Δ ggt) mutant to release p-nitroanilide from Lγ-glutamyl-p-nitroanilide, as a result of the activity of the enzyme GGT and thereby confirms that the ggt gene in *F. tularensis* does in fact encode gamma glutamyl transferase. Surprisingly, the deletion or silencing of this gene attenuates the bacteria.

FIG. 4 shows that the ggt deleted (Δ ggt) mutant recovered from a macrophage cell line in an in vitro assay is significantly lower than the amount of SCHU S4, thereby providing further evidence the Δ ggt is attenuated. The assay is a measure of the ability of the bacteria to infect the macrophages and the effect of the same on the survival of the macrophages.

What is more the deletion of the ggt gene results in a significantly attenuated bacterium in vivo. FIG. 5 shows that the median lethal dose of the ggt deleted (Δ ggt) mutant is $2 \times 10^6$ CFU (colony forming units) in contrast to wild-type which has a median lethal dose of 1 CFU. Thus the activity of the mutant is attenuated by more than 1 million fold, which is very surprising.

Attenuated as employed herein means the bacteria has reduced virulence with respect to wild-type bacteria, for example with respect to SCHU S4. In particular, a 10, 20, 30, 40, 50, 60, 70, 80% or reduction in virulence.

SCHU S4 is a human isolate, the sequence for which is disclosed in Larsson, P; Oyston, et al. *The complete genome sequence of Francisella tularensis, the causative agent of tularemia*. Nat Genet. 2005; 37:153-159.

Reduced virulence as employed herein, may be measured by, for example the median lethal dose of bacteria required in mice such as Balb/C mice. Thus where the CFU value required for a ggt deleted/silenced mutant is higher than the CFU value for the wild-type in the median lethal dose assay, the ggt deleted mutant can be considered less virulent and therefore attenuated. In one embodiment the CFU value of the ggt deleted/silenced mutant is 2, 5, 10, 50, 100, 200, 300, 400, 500, 600, 700, 800, 900, 1,000, 5,000, 1,000,000, 2,000,000 or more times that of the wild-type. Thus in one embodiment the attenuation is the reciprocal of the fold increase in the CFU value.

Where the median lethal dose in CFUs for the ggt deleted or silenced mutant is 1,000 or more times the value of the wild-type then the mutant can be considered to be significantly or highly attenuated.

The mutant is also advantageous in that it simultaneously retains its immunogenic properties. This makes the attenuated bacteria suitable for use in a vaccine. Thus the mutant according to the invention provides protection in vivo when administered at appropriate doses. Protective properties of attenuated strains cannot be predicted. In some instances strains can be "over attenuated" in that they have an acceptable median lethal dose but give no protection or inadequate protection to challenge with a virulent strain such the clinically relevant strain SCHU S4.

FIG. 6 shows that mice vaccinated with the ggt deleted (Δ ggt) mutant at various doses, were protected against challenge with 100 CFU (equivalent to 100× the median lethal dose) of a fully virulent wild-type strain. The level of protection afforded by the mutant strain was reduced when a lower dose of the mutant was used for the inoculation.

In a given bacterium a deleted ggt gene as used herein refers to where part or all of the gene has been deleted and the function of the particular ggt gene, at least in relation to the enzyme GGT, is eliminated or reduced (for example the gene can no longer be used to generate the GGT enzyme) and/or the GGT enzyme activity is eliminated or reduced (for example because the enzyme has not been synthesised or because the protein synthesised does not have the required enzyme activity).

Reduced function as employed in relation to deleted or silenced genes refers to where the GGT activity is reduced, 10, 20, 30, 40, 50, 60, 70, 80, 90% or more (such as 100%) in comparison to the GGT produced by the corresponding unmutated bacterium, for example as measured by release of p-nitroanilide from Lγ-glutamyl-p-nitroanilide, in particular as described herein.

Silenced as employed herein includes any mechanism other than deletion for eliminating or reducing the function of the relevant gene, for example a non-natural polynucleotide sequence (for example DNA) can be inserted in the gene to disrupt the function. A silenced gene includes a transposon mutant. Alternatively, the gene can be excised and re-inserted in a transposed orientation to render it non-functional. In a further alternative the start codon of the ggt gene may be deleted or silenced such that the gene is silenced as a result of failure to be transcribed.

Alternative mechanisms for silencing the gene include RNAi technology (also referred to as RNA inactivating). The technique is suitable for inactivating genes in a cell through the introduction of double-stranded RNA into the cell. RNA inactivation is based on the phenomenon that animal cells destroy RNA when they meet it in the form of a double strand. If a segment of double-stranded RNA has the same sequence as part of a gene, it triggers the destruction of the messenger RNA (mRNA) produced by that gene, effectively silencing it. Double-strand RNA can directly suppress and silence a target gene. In some embodiments a bacterium of the invention is modified to co-express an RNAi component corresponding to the ggt gene.

The invention also extends to a population of bacteria mutated as described herein, for example wherein 40, 50, 60, 70, 80, 90, 95, 96, 97, 98, 99 or 100% of the bacteria have the characteristics of a bacterium described herein. In one embodiment the population is in a substantially isolated and/or purified form.

In one embodiment part of all of the ggt gene is deleted, for example the entire gene is deleted, as described herein.

In one embodiment the mutant is derived from:
tularensis (for example tularensis; holarctica such as Biovar I, II or III; or mediasiatica) novicida or philomiragia (for example noatunesis and philomiragia),
in particular tularensis for example tularensis; holarctica such as Biovar I, II or III
especially tularensis tularensis.

In one embodiment the attenuated bacterium according to the disclosure is derived from strain SCHU S4.

Derived from as employed herein is intended to refer to where the desired bacterium is prepared by mutating the original strain or is prepared by replicating genetic material obtained directly or indirectly from the original strain, for example employing recombinant methods.

In one embodiment the disclosure does not extend to a bacterium derived from the LVS strain with a deleted or silenced ggt gene. In particular, transposon insert mutants of LVS, wherein the insert is in the ggt gene may be excluded from the scope of the present disclosure.

In one embodiment the disclosure does not extend to transposon insert mutants wherein the insert is in the ggt gene.

In one embodiment the attenuated mutant strain of the disclosure has at least one activity 100, 1000, 10,000 or 1,000,000 times less than that of a wild-type tularensis. Examples of activities are those described herein, such as virulence, in particular median lethal dose.

Wild-type as employed herein is intended to refer to naturally occurring virulent strains of the bacteria, in particular tularensis tularensis, in particular SCHU S4.

In one embodiment the mutant of the disclosure has a median lethal dose of at least 100 CFU, such as 1000 CFU, such as $1 \times 10^6$ CFU, in particular $2 \times 10^6$ CFU, for example as measured by dosing mice subcutaneously (sc) with serial dilutions of bacteria in PBS (phosphate buffered saline). The concentration of bacteria in the inoculum may determined by retrospective viable count.

In one embodiment the mutant has a one or more further genes (such as 1 or 2) deleted or silenced, for example genes involved in cycles essential to growth and/or replication, in particular genes upregulated when the bacterium is infecting a host, for example genes selected from feoB, pilV, FTT_1144, lysA, FTT_0026, dnaN, pyrF, ostA2, FTT_0580, FTT_0582, sufB, FTT_1191, bfr, lysA, FTT_0536, pyrD, FTT_0847, FTT_0749, coaD, sufB, rubA, FTT_0103, frgA, FTT_0028, FTT_0026, trpB, ppdK, FTT_1618, glyQ, FTT_0516, ptsN, rnfB, thrS, FTT_1693, FTT_1361, FTT_0978, FTT_1068, galU, dxs, FTT_0672, FTT_0628, FTT_0613, ispF, FTT_0613, fabH, FTT_0497, FTT_1381, feoA, sdhC, nuoA and mixtures thereof.

In particular, one or more genes (such as 1 or 2) are deleted or silenced which are upregulated when the bacteria are deprived of iron, for example selected from feoB, pilV, FTT_1144, lysA, FTT_0026, dnaN, pyrF, ostA2, FTT_0580, FTT_0582, sufB, FTT_1191, hfr, lysA, FTT_0536, pyrD, FTT_0847, FTT_0749, coaD, sufB, rubA, FTT_0103, frgA, FTT_0028, and trpB.

In one embodiment the deleted gene or genes has a fold change value of 1.5 to 10 such as 1.5 to 5, when analysed by microarray analysis. The fold change is a statistical measure of the differential expression of genes analysed in different experiments, to allow the comparison of the results there from.

In one embodiment the deleted gene or genes has a p value less than 1, for example less than 0.5, such 0.05 or less. The p value is also a statistical measure of the extent to which a gene is differentially expressed.

In one or more embodiments of the disclosure the bacterium is an auxotroph for cysteine. In an alternative aspect there is a provided an attenuated Francisella bacterium, wherein two or more genes upregulated during infection of a host, growth and/or replication are deleted or silenced, in particular combinations of genes selected from Table 1. The deletion or silencing of the gene may be detected indirectly by, for example monitoring the activity of a protein encoded by the gene. When the gene is deleted the bacteria obtained can be sequenced to confirm the absence of the relevant gene. Alternatively, DNA analytical techniques include Southern Blot and PCR. In one embodiment at least one gene is ggt.

In one embodiment there is provided a formulation, such as a pharmaceutical composition comprising an attenuated bacterium as described herein (in particular a therapeutically effective amount thereof), and an excipient, for example a diluent or carrier.

There is further provided by the present disclosure a process of preparing a pharmaceutical composition, which process comprises mixing a bacterium of the disclosure, together with a pharmaceutically acceptable excipient, diluent and/or carrier.

The bacterium of the disclosure may be formulated for administration in any convenient way for use in human or veterinary medicine. Such compositions may be presented for use in a conventional manner with the aid of one or more suitable excipients, diluents and/or carriers. Acceptable excipients, diluents and carriers for therapeutic use are well known in the pharmaceutical art, and are described, for example, in Remington's Pharmaceutical Sciences, Mack Publishing Co. (A. R. Gennaro edit. 1985). The choice of pharmaceutical excipient, diluent and/or carrier can be selected with regard to the intended route of administration and standard pharmaceutical practice. The pharmaceutical compositions may comprise as (or in addition to) the excipient, diluent and/or carrier any suitable binder(s), lubricant(s), suspending agent(s), coating agent(s), solubilising agent(s).

Preservatives, stabilisers, dyes and/or flavouring agents may be provided in the pharmaceutical composition. Examples of preservatives include sodium benzoate, sorbic acid and esters of p-hydroxybenzoic acid. Antioxidants and suspending agents may be also used. For some embodiments, the agents of the present disclosure may also be used in combination with a cyclodextrin. Cyclodextrins may form inclusion and non-inclusion complexes with the active entity (ie the bacterium). Formation of an, active-cyclodextrin complex may modify the solubility, dissolution rate, bioavailability and/or stability property of the active. The complexes are generally useful for most dosage forms and administration routes. As an alternative to direct complexation with the active the cyclodextrin may be used as an auxiliary additive, e.g. as a carrier, diluent or solubiliser. Alpha-, beta- and gamma-cyclodextrins are most commonly used and suitable examples are described in WO 91/11172, WO 94/02518 and WO 98/55148.

The routes for administration (delivery) include, but are not limited to, one or more of: oral rectal, buccal, and sublingual (e.g. as a dry powder/free flowing particulate formulation, tablet, capsule, or as a solution or suspension, as appropriate).

In some instances it may be possible to deliver the bacterium and formulations of the disclosure by a topical route, for example by inhalation or delivery to mucosal membrane (e.g. as a nasal spray or aerosol for inhalation), nasal, parenteral (e.g. by an injectable form such as intraperitoneal, intramuscular, intravenous, intradermal, subcutaneous), or a transdermal route. Of course there may be different formulation requirements depending on the different delivery systems.

Where appropriate, the pharmaceutical compositions can be administered, parenterally, for example intravenously, intramuscularly or subcutaneously. For parenteral administration, the compositions may be best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

The compositions of the disclosure include those in a form especially formulated for parenteral, buccal, topical, implant, dermal delivery or nasal use.

The tablets may contain excipients such as microcrystalline cellulose, lactose, sodium citrate, calcium carbonate, calcium sulphate, dibasic calcium phosphate and glycine, mannitol, pregelatinised starch, corn starch, potato starch, disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and/or acacia.

Additionally, lubricating agents such as magnesium stearate, stearic acid, glyceryl behenate and/or talc may be included.

Solid compositions of a similar type may also be employed as fillers in gelatin or HPMC (hydroxypropyl methylcellulose) capsules. Suitable excipients in this regard include microcrystalline cellulose, lactose, calcium carbonate, calcium sulphate, dibasic calcium phosphate and/or, mannitol, pregelatinised starch, corn starch, potato starch and/or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and/or glycerin, and combinations thereof.

The bacterium or formulations of the disclosure may also be used in combination with other therapeutic agents in particular one or more antibiotics, for example gentamicin, tetracycline-class drugs such as doxycycline, chloramphenicol and/or fluoroquinolones. The combination may be provided as a co-formulation or simply packaged together as separate formulations, for simultaneous or sequential delivery, including delivery by separate routes.

In one embodiment the mutant bacterium as defined herein is employed in combination with one or more further antigens.

In one embodiment the formulation according to the disclosure is a vaccine formulation.

The formulation according to the disclosure may be lyophilized for reconstitution later or alternatively may be provided as a liquid formulation. Optionally the formulation may comprise an adjuvant, for example an adjuvant formulation may be used to reconstitute a lyophilized formulation.

In one embodiment the bacterium is employed in a prime boost regime, as the priming and/or boosting dose. In certain embodiments the prime boost may be a heterologous regime. Vaccines may be delivered via a variety of routes. Typical delivery routes include parenteral administration, e.g., intradermal, intramuscular or subcutaneous delivery. Although other routes including oral, administration, intranasal, and intravaginal routes, may be employed.

Transdermal administration, such as by iontophoresis, may also be an effective method to deliver the bacterium of the disclosure. The disclosure also extends to delivery by a transdermal patch, which may be occlusive or non-occlusive.

Vaccines can also be formulated for administration via the nasal passages. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. For further discussions of nasal administration of AIDS-related vaccines, references are made to the following patents, U.S. Pat. Nos. 5,846,978, 5,663,169, 5,578,597, 5,502,060, 5,476,874, 5,413,999, 5,308,854, 5,192,668, and 5,187,074.

In one embodiment the formulation is provided as a sterile suspension or emulsion. In such compositions the relevant active ingredient may be in admixture with a suitable carrier, diluent, or excipient such as sterile water, physiological saline, glucose or the like. The bacterium may be incorporated, if desired, into liposomes, microspheres or other polymer matrices (Felgner et al., U.S. Pat. No. 5,703,055; Gregoriadis, Liposome Technology, Vols. I to III (2nd ed. 1993), each of which is incorporated herein by reference). Liposomes, for example, which consist of phospholipids or other lipids, are nontoxic, physiologically acceptable and metabolizable carriers that are relatively simple to make and administer.

Liposome carriers may serve to target a particular tissue or infected cells, as well as increase the half-life of the vaccine. Liposomes include emulsions, foams, micelles, insoluble monolayers, liquid crystals, phospholipid dispersions, lamellar layers and the like. In these preparations the bacterium to be delivered is incorporated as part of a liposome, alone or in conjunction with a molecule which hinds to, e.g., a receptor, such as monoclonal antibodies, or with other therapeutic or immunogenic compositions. Thus, liposomes either filled or decorated with a desired immunogen of the disclosure can be directed to the site of lymphoid cells, where the liposomes then deliver the immunogen(s). Liposomes may be formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., Ann. Rev. Biophys. Bioeng. 9:467 (1980), U.S. Pat. Nos. 4,235,871, 4,501,728, 4,837,028, and 5,019,369.

The liposomes generally contain a neutral lipid, for example phosphatidylcholine, which is usually non-crystalline at room temperature, for example eggyolk phosphatidylcholine, dioleoyl phosphatidylcholine or dilauryl phosphatidylcholine.

The bacterium according to the disclosure may be mixed or adsorbed with adjuvants, which include but are not limited to alum, muramyl dipeptide and/or saponins such as Quil A.

Particular adjuvants are those selected from the group of metal salts, oil in water emulsions, Toll like receptors agonist, (in particular Toll like receptor 2 agonist, Toll like receptor 3 agonist, Toll like receptor 4 agonist, Toll like receptor 7 agonist, Toll like receptor 8 agonist and Toll like receptor 9 agonist), saponins or combinations thereof. The level of free antigen in a given formulation may be increased by, for example, formulating the composition in the presence of phosphate ions, such as phosphate buffered saline, or by increasing the ratio of antigen to metal salt. In one embodiment the adjuvant does not include a metal salt as sole adjuvant. In one embodiment the adjuvant does not include a metal salt.

In an embodiment the adjuvant is a Toll like receptor (TLR) 4 ligand, for example an agonist such as a lipid A derivative, in particular monophosphoryl lipid A or more specifically 3-deacylated monophoshoryl lipid A (3D-MPL).

3-Deacylated monophosphoryl lipid A is known from U.S. Pat. No. 4,912,094 and UK patent application No. 2,220,211 (Ribi) and is available from Ribi Immunochem, Montana, USA.

3D-MPL is sold under the trademark MPL® by Corixa corporation and primarily promotes CD4+ T cell responses with an IFN-g (Th$_1$) phenotype. It can be produced according to the methods disclosed in GB 2 220 211 A. Chemically it is a mixture of 3-deacylated monophosphoryl lipid A with 3, 4, 5 or 6 acylated chains. Generally in the compositions of the present invention small particle 3D-MPL is used. Small particle 3D-MPL has a particle size such that it may be sterile-filtered through a 0.22 µm filter. Such preparations are described in International Patent Application No. WO 94/21292.

Synthetic derivatives of lipid A are known and thought to be TLR 4 agonists including, but not limited to:

OM174 (2-deoxy-6-O-[2-deoxy-2-[(R)-3-dodecanoyloxytetra-decanoylamino]-4-o-phosphono-β-D-glucopyranosyl]-2-[(R)-3-hydroxytetradecanoyl amino]-α-D-glucopyranosyldihydrogenphosphate), (WO 95/14026).

OM 294 DP (3S,9R)-3-[(R)-dodecanoyloxytetradecanoylamino]-4-oxo-5-aza-9(R)-[(R)-3-hydroxytetradecanoylaminodecan-1,10-diol,1,10-bis(dihydrogenophosphate) (WO 99/64301 and WO 00/0462).

OM 197 MP-Ac DP (3S-,9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127).

Typically when 3D-MPL is used the antigen and 3D-MPL are delivered with alum or presented in an oil in water emulsion or multiple oil in water emulsions. The incorporation of 3D-MPL is advantageous since it is a stimulator of effector T-cell responses. Alternatively the 3D-MPL may be formulated as liposomes.

Other TLR4 ligands which may be used are alkyl Glucosaminide phosphates (AGPs) such as those disclosed in WO 9850399 or U.S. Pat. No. 6,303,347 (processes for preparation of AGPs are also disclosed), or pharmaceutically acceptable salts of AGPs as disclosed in U.S. Pat. No. 6,764, 840. Some AGPs are TLR4 agonists, and some are TLR4 antagonists. Both are thought to be useful as adjuvants.

Another immunostimulant for use in the present formulations is Quil A and its derivatives. Quil A is a saponin preparation isolated from the South American tree Quilaja Saponaria Molina and was first described as having adjuvant activity by Dalsgaard et al. in 1974 ("Saponin adjuvants", Archiv. fur die gesamte Virusforschung, Vol. 44, Springer Verlag, Berlin, p 243-254). Purified fragments of Quil A have been isolated by HPLC which retain adjuvant activity without the toxicity associated with Quil A (EP 0 362 278), for example QS7 and QS21 (also known as QA7 and QA21). QS21 is a natural saponin derived from the bark of Quillaja saponaria Molina which induces CD8+ cytotoxic T cells (CTLs), Th$_1$ cells and a predominant IgG2a antibody response.

Particular formulations of QS21 have been described which further comprise a sterol (WO 96/33739). The ratio of QS21:sterol will typically be in the order of 1:100 to 1:1 weight to weight.

Generally an excess of sterol is present, the ratio of QS21:sterol being at least 1:2 w/w. Typically for human administration QS21 and sterol will be present in a vaccine in the range of about 1 µg to about 100 µg, such as about 10 µg to about 50 µg per dose.

A formulation comprising QS21 and liposomes may be prepared, for example containing a charged lipid, which increases the stability of the liposome-QS21 structure for liposomes composed of saturated lipids. In these cases the amount of charged lipid is often 1-20% w/w, such as 5-10%. The ratio of sterol to phospholipid is 1-50% (mol/mol), such as 20-25%. These compositions may contain MPL (3-deacylated mono-phosphoryl lipid A, also known as 3D-MPL).

The saponins may be separate in the form of micelles, mixed micelles (generally, but not exclusively with bile salts) or may be in the form of ISCOM matrices (EP 0 109 942 B1), liposomes or related colloidal structures such as worm-like or ring-like multimeric complexes or lipidic/layered structures and lamellae when formulated with cholesterol and lipid, or in the form of an oil in water emulsion (for example as in WO 95/17210). The saponins may often be associated with a metallic salt, such as aluminium hydroxide or aluminium phosphate (WO 98/15287).

Usually, the saponin is presented in the form of a liposome, ISCOM or an oil in water emulsion.

Immunostimulatory oligonucleotides may also be used. Examples of oligonucleotides for use in adjuvants or vaccines of the present invention include CpG containing oligonucleotides, generally containing two or more dinucleotide CpG motifs separated by at least three, more often at least six or more nucleotides. A CpG motif is a cytosine nucleotide followed by a guanine nucleotide. The CpG oligonucleotides are typically deoxynucleotides. In one embodiment the internucleotide in the oligonucleotide is phosphorodithioate, or more preferably a phosphorothioate bond, although phosphodiester and other internucleotide bonds are within the scope of the invention. Also included within the scope of the disclosure are oligonucleotides with mixed internucleotide linkages. Methods for producing phosphorothioate oligonucleotides or phosphorodithioate are described in U.S. Pat. No. 5,666,153, U.S. Pat. No. 5,278,302 and WO 95/26204.

Examples of oligonucleotides are as follows: TCC ATG ACG TTC CTG ACG TT (CpG 1826) (SEQ ID NO:1)
TCT CCC AGC GTG CGC CAT (CpG 1758) (SEQ ID NO:2)
ACC GAT GAC GTC GCC GGT GAC GGC ACC ACG (SEQ ID NO:3)
TCG TCG TTT TGT CGT TTT GTC GTT (CpG 2006) (SEQ ID NO:4)
TCC ATG ACG TTC CTG ATG CT (CpG 1668) (SEQ ID NO:5)
TCG ACG TTT TCG GCG CGC GCC G (CpG 5456) (SEQ ID NO:6),
the sequences may contain phosphorothioate modified internucleotide linkages. Alternative CpG oligonucleotides may comprise one or more sequences above in that they have inconsequential deletions or additions thereto.

The CpG oligonucleotides may be synthesized by any method known in the art (for example see EP 468520). Conveniently, such oligonucleotides maybe synthesized utilising an automated synthesizer.

Examples of a TLR 2 agonist include peptidoglycan or lipoprotein. Imidazoquinolines, such as Imiquimod and Resiquimod are known TLR7 agonists. Single stranded RNA is also a known TLR agonist (TLR8 in humans and TLR7 in mice), whereas double stranded RNA and poly IC (polyinosinic-polycytidylic acid—a commercial synthetic mimetic of viral RNA) are exemplary of TLR 3 agonists. 3D-MPL is an example of a TLR4 agonist whilst CpG is an example of a TLR9 agonist.

An immunostimulant may alternatively or in addition be included. In one embodiment this immunostimulant will be 3-deacylated monophosphoryl lipid A (3D-MPL).

Adjuvants combinations include 3D-MPL and QS21 (EP 0671 948 B1), oil in water emulsions comprising 3D-MPL and QS21 (WO 95/17210, WO 98/56414), or 3D-MPL formulated with other carriers (EP 0 689 454 B1) including liposomes. Other adjuvant systems comprise a combination of 3D-MPL, QS21 and a CpG oligonucleotide as described in U.S. Pat. No. 6,558,670 and U.S. Pat. No. 6,544,518.

in one aspect the adjuvant comprises 3D-MPL.
In one aspect the adjuvant comprises QS21.
In one aspect the adjuvant comprises CpG.
In one aspect the adjuvant comprises QS21 and 3D-MPL.
In one aspect the adjuvant comprises QS21, 3 D-MPL and CpG In one aspect the adjuvant is formulated as an oil in water emulsion.

In one aspect the adjuvant is formulated as liposomes.

The amount of 3D-MPL used is generally small, but depending on the vaccine formulation may be in the region of 1 to 1000 µg per dose, generally 1 to 500 µg per dose, and more such as between 1 to 100 µg per dose (10, 20, 30, 40, 50, 60, 70, 80 or 90 µg per dose).

The amount of CpG or immunostimulatory oligonucleotides in the adjuvants or vaccines of the present invention is generally small, but depending on the vaccine formulation maybe in the region of 1 to 1000 µg per dose, generally 1 to 500 µg per dose, and more such as between 1 to 100 µg per dose (10, 20, 30, 40, 50, 60, 70, 80 or 90 µg per dose).

The amount of saponin for use in the adjuvants of the present invention may be in the region of 1 to 1000 µg per dose, generally 1 to 500 µg per dose, more such as 1 to 250 µg per dose, and more specifically between 1 to 100 µg per dose (10, 20, 30, 40, 50, 60, 70, 80 or 90 µg per dose).

Vaccine preparation is generally described in New Trends and Developments in Vaccines, edited by Voller et al., University Park Press, Baltimore, Md., U.S.A., 1978. Encapsulation within liposomes is described, for example, by Fullerton, U.S. Pat. No. 4,235,877.

The dose of bacterium employed may be in the range $1\text{-}10\times10^2$ CFU to about $1\text{-}10\times10^{10}$ CFU such as 1-10 in particular 2, 3, 4, 5, 6, 7, 8, $9\times10^3$ to $10^6$ CFU.

If the vaccine of the invention comprises a further antigen/immunogen the amount in each vaccine dose will be selected as an amount which induces an immunoprotective response without significant, adverse side effects in typical vaccines. Such amount will vary depending upon which specific immunogen is employed and whether or not the vaccine is adjuvanted. Generally, it is expected that each does will comprise 1 to 1000 µg of antigen, for example 1-200 µg such as 10-100 µg more particularly 10-40 µg. An optimal amount for a particular vaccine can be ascertained by standard studies involving observation of antibody titres and other responses in subjects. Following an initial vaccination, subjects may for example receive a boost, for example in about 4 weeks, which may be followed by repeated boosts every six months for as long as a risk of infection exists.

Thus when a bacterium or composition of the disclosure is used in combination with a second therapeutic agent active against the same disease state the dose of each compound may differ from that when used alone. Appropriate doses will be readily appreciated by those skilled in the art. It will also be appreciated that the dose required for use in treatment will vary with the nature of the condition being treated and the age and the condition of the patient and will be ultimately at the discretion of the attendant physician or veterinarian.

The compositions may contain from 0.01-99% of the active material. For topical administration, for example, the composition will generally contain from 0.01-10%, more specifically 0.01-1% of the active material.

In one or more aspects the immune response provided when the invention is employed may be a cell based immune response, for example a CD4 and/or CD8 response.

In one embodiment an antibody response is generated, for example in addition to other immune responses generated or as an alternative response, for example an IgG response.

In one embodiment a vaccine according to the present disclosure provides protective immunity to challenge with virulent *F. tularensis*, in particular 10 or 100 times the median lethal dose of a virulent strain, such as SCHU S4.

In one aspect there is provided an attenuated bacterium or composition as described herein for use in therapy, for example the treatment or prophylaxis of tularemia.

In one aspect there is provided use of an attenuated bacterium or composition as described herein in the manufacture of a medicament for the treatment or prophylaxis of tularemia.

In one aspect there is provided a method of therapy comprising the step of administering a therapeutically effective amount of a bacterium or composition as described herein to a patient in need thereof, for example for the prophylaxis or treatment of tularemia Therapy as employed herein is intended to refer to treatment and/or prophylaxis.

Prophylaxis as employed herein refers to treatment before infection with the pathogen F. tularensis, thereby preventing subsequent infection (protective immunity) or reducing the severity and/or duration of the symptoms of the invention.

Treatment as employed herein is intended to refer to administration post infection with the pathogen F. tularensis with the aim of ameliorating or curing the symptoms thereof.

The disclosure included a method of preparing a bacterium as described herein comprising the step of deleting or silencing at least the ggt, gene and optionally one or more further genes, and the product obtainable therefrom.

In one embodiment there is provided a process for the culturing a bacterium as described here, in particular comprising the step of replicating the bacterium. In one aspect the process comprises the step of providing a source of cysteine for metabolism by the growing and/replicating bacteria. The bacteria according to the invention may cultured in a variety of media, for example blood, cysteine, glucose agar (BCGA), solidified Chamberlain's Defined medium (CDM), or Thayer-Martin agar, at a suitable temperature such as about 37° C. In some instances it may be desirable to grow the bacteria in serum free media.

The process may comprise the further optional step of purifying the bacteria therefrom. Purification may, for example comprise the steps of removing the bacteria from the media, such as BCGA, and suspending in a buffer, such as phosphate saline buffer. Suitable methods of removing the bacteria from the media include centrifugation, filtration or the like.

The process may also comprise the further step of admixing the mutant bacteria obtained with one or more pharmaceutical excipients.

In the context of this specification "comprising" is to be interpreted as "including".

Aspects of the invention comprising certain elements are also intended to extend to alternative embodiments "consisting" or "consisting essentially" of the relevant elements.

The disclosure also extends to combinations of embodiments, as technically appropriate.

EXAMPLES

An isogenic mutant for ggt was generated in the highly virulent type A F. tularensis strain SCHU S4. In order to confirm the function of ggt in a fully virulent isolate the effect of this mutation on GGT activity was investigated. To confirm that this mutation was attenuating in a highly virulent strain, the ability of bacteria to infect macrophages and mice was also investigated. The protective efficacy of this mutant against a fully virulent SCHU S4 challenge was also evaluated. The ability of the mutant to synthesise cysteine from GSH has also been investigated.

Bacterial Strains and Culture Conditions

The bacterial strains used in this study are listed in Table A. Strains of F. tularensis were grown routinely on blood cysteine glucose agar supplemented with 4% cysteine, 4% histidine, 5% glucose and 10% fresh filtered horse blood (BCGA), solidified Chamberlain's Defined medium (CDM) (Chamberlain, R. E. 1965. Evaluation of live tularemia vaccine prepared in a chemically defined medium. Appl. Microbiol. 13:232-235) or Thayer-Martin agar (Atlas, R. M. 2004. Handbook of Microbiological Media, Third Edition. Coordinating ed., L. C. Parks. CRC Press, Florida, USA). Where required, media were supplemented with 100 µg/ml polymyxin and 12.5 µg/ml kanamycin. Strains of E. coli were grown in Luria-Bertani (LB) medium (see Atlas. R. M above) or on LB agar at 37° C., supplemented as required with 25 µg/ml kanamycin. All work undertaken with Francisella strains was performed under appropriate laboratory containment conditions in accordance with relevant legislative requirements.

Plasmids and Manipulation of DNA

Generally, the manipulation of DNA was carried out as outlined previously (Sambrook, J. and D. W. Russell. 2001. Molecular cloning: a laboratory manual. Cold Spring Harbor Laboratory Press). Genomic DNA was isolated using the Gentra® Puregene® DNA Isolation kit (QIAGEN® Ltd., Crawley, UK). Plasmid DNA was isolated using QIAGEN Plasmid Mini and Maxi Kits. Plasmids used in this study are shown in Table A. Southern blotting was performed under high-stringency conditions as detailed by Sambrook and Russell (see Sambrook, J. and D. W. Russell. 2001 above). Standard PCR was performed with 25 cycles of 94° C. 30 s, 50° C. 30 s, 72° C. 30 s.

TABLE A

Bacterial strains and plasmids used in this study.

| Strain/plasmid | Description | Source |
|---|---|---|
| Strains | | |
| Escherichia coli | | |
| JM109 | Host cloning strain | Promega* |
| S17-λpir | Host strain used for transfer of suicide plasmid into F. tularensis SCHU S4 by conjugation | |
| F. tularensis | | |
| SCHU S4 | Wild type F. tularensis subsp. tularensis strain F. tularensis SCHU S4 with unmarked, in-frame deletion of ggt | FSC237 |
| SCHU S4 Δggt | | This study |
| Plasmids | | |
| pGEM•-T Easy Vector System I | Cloning vector, Amp$^R$ | Promega |
| pSMP75 | Suicide vector containing sacB selection gene; Kan$^R$ pSMP75 containing 1787 bp Δggt left and right flanking regions inserted at MluI site | This study |
| pSMP75Δggt | | This study |

*Simon, R., U. B. Priefer, and A. Puhler. 1983. A broad host range mobilisation system for in vitro genetic engineering: transposon mutagenesis in Gram-negative bacteria. Biotechnology 1: 784-791.

Generation of a F. tularensis Δggt Mutant

To determine the function of GGT in F. tularensis, a mutant was constructed in strain SCHU S4. PCR and Southern blot analysis confirmed the double crossover and successful allelic replacement of the gene (data not shown). The same Southern blot analysis also confirmed that only one copy of the ggt gene was encoded in the genome. The genome sequence of strain SCHU S4 shows that ggt is flanked by two pseudogenes, FTT1180 and vacJ, making it unlikely that allelic replacement of ggt would have any polar effect on flanking genes.

Primers were designed from the genome sequence of strain SCHU S4, such that a 1787 bp deletion was generated in the ggt (FTT1181c) open reading frame. Primers were used to amplify DNA regions flanking the deletion (left flank forward, ggtF1: 5'-ACGCGTTAGGTTACCTTGGGCTTGAG-3' (SEQ ID NO:7); reverse, ggtR1: 5'-AGATCTGGTTAT-TAAACACTTTAATAG-3' (SEQ ID NO:8); right flank forward, ggtF2: 5'-AGATCTACGACGCATTAAAGAAAC-3' (SEQ ID NO:9), reverse, ggtR2: 5'-ACGCGTTGTGG-GATTAAGTGGGAAACC-3' (SEQ ID NO:10)). These amplicons were ligated with pGEM-T Easy (Promega UK Ltd., Southampton, UK) according to the manufacturer's protocol to generate pGEMggt1 and pGEMggt2 containing left and right flanks respectively. The plasmids were digested with Bgl2 to linearise both plasmids which were then ligated. The ligated plasmids were used as template in a PCR to join the two flanks, using primers ggtF1 and ggtR2. The product was ligated with pGEM-T Easy as above and used to transform E. coli JM109. Plasmids were isolated and the correct sequence confirmed by PCR. One correct clone was digested with MluI and the insert isolated and ligated with similarly digested pSMP75 to produce pSM75Δggt. Plasmid pSM75Δggt was introduced into F. tularensis strain SCHU S4 by conjugation using the method of Golovliov et al. (Golovliov, I., A. Sjostedt, A. Mokrievich, and V. Pavlov. 2003. A method for allelic replacement in Francisella tularensis. FEMS Microbiol. Lett. 222:273-280.). Briefly, E. coli S17λpir pSM75Δggt was grown overnight in LB-kanamycin, then a 1 ml aliquot was removed, the bacteria sedimented by centrifugation and resuspended in 50 μl fresh LB broth. The Francisella were grown on BCGA overnight at 37° C. in a confluent lawn. Bacteria were removed using a sterile loop and resuspended in the E. coli suspension, and the mixture spotted onto BCGA. After incubation overnight at 25° C. the bacteria were removed with a sterile loop and resuspended in 500 μl A PBS before being inoculated onto Thayer-Martin agar supplemented with 100 μg/ml polymyxin (to inhibit growth of the E. coli) and 12.5 μg/ml kanamycin. Colonies were subcultured onto Thayer-Martin agar supplemented with 5% sucrose. Isolated colonies which grew in the presence of sucrose were analysed by PCR for the deletion of the ggt open reading frame and loss of the vector. This was subsequently confirmed by Southern blotting. The strain was designated F. tularensis SCHU S4 Δggt.

Assay for GGT Activity

The GGT activity of both mutant and wild type F. tularensis strains was determined by measuring optically the release of p-nitroanilide from L-γ-glutamyl-p-nitroanilide as described previously with minor modifications (Huseby, N. F. and J. H. Strömme. 1974. Practical points regarding routine determination of γ-glutamyl transferase (γ-GT) in serum with a kinetic method at 37° C. Scand. J. Clin. Lab. Invest. 34:357-363.). Briefly, reaction buffer consisting of 1 mM L-γ-glutamyl-p-nitroanilide, 20 mM Gly-Gly, and 60 mM Tris-HCL (pH 8.0) was prepared and 180 μl applied to each well of a 96-well microtitre plate. Bacteria were suspended in PBS to an OD590 of 0.6 and 20 μl also applied to each well. Assays were performed at 37° C. for 23 hours, and which point the absorbance at 405 nm of each well was measured. The results are shown in triplicate in FIG. 2.

GGT activity was observed to be on average approx. 11-fold higher in strain SCHU S4 than in SCHU S4 Δggt (T-test p-value=0.020). This result demonstrates that, the ggt of SCHU S4 does encode GGT. Growth of the mutant and wild type strains in vitro was comparable suggesting that GGT is not essential for in vitro growth of F. tularensis (data not shown). The expression of active GGT by the wild type strain cultured in vitro seems to indicate that, although not essential, GGT may still contribute to the ability of F. tularensis to overcome growth limiting factors.

Growth in the Absence of Exogenous Cysteine

Overnight cultures of bacteria on BCGA were suspended in PBS and used to inoculate media to a starting OD590 of 0.14. Cultures were incubated at 37° C. with shaking at 150 rpm for 19 hours, following which the OD590 was measured as an indication of bacterial growth. Growth was measured in the following media: CDM, CDM prepared without cysteine (CDM-cys), CDM-cys supplemented with 0.6 mM GSH, and CDM-cys supplemented with 1.3 mM GSH.

To test whether GGT in F. tularensis SCHU S4 plays a role in the synthesis of cysteine from GSH, the growth of SCHU S4 and SCHU S4 Δggt were compared in vitro in cysteine-depleted media that was supplemented with GSH. The results of triplicate assays are shown in FIG. 3. The growth of both the wild type and mutant was reduced by approx. 8-fold in CDM-cys compared to CDM. The addition of 0.6 mM GSH to the media restored the growth of SCHU S4 to a similar level to that observed in CDM, whereas the growth of SCHU S4 Δggt was only partially restored, to 2.1-fold that of growth in CDM. Partial restoration of the growth of SCHU S4 Δggt upon supplementation with GSH was unexpected, and may have indicated partial spontaneous degradation of GSH, resulting in contamination with free cysteine molecules. To test whether or not this was the case, the experiment was repeated using 1.3 mM GSH on the premise that this would introduce additional free cysteine and thus further restore growth of SCHU S4 Δggt. The growth of SCHU S4 Δggt in CDM-cys remained at similar levels upon the addition of both 0.6 mM and 1.3 mM GSH, indicating that free cysteine was not the cause of the restored growth of the mutant (FIG. 3).

Macrophage Assay

Bacterial survival in J774.A1 murine macrophages was studied using the method described by Golovliov et al. (Golovliov, I., M. Ericsson, G. Sandström, A. Tärnvik, and A. Sjöstedt. 1997. Identification of proteins of Francisella tularensis induced during growth in macrophages and cloning of the gene encoding a prominently induced 23-kilodalton protein. Infect. Immun. 65:2183-2189.), using a multiplicity of infection (MOI) of ten. Briefly, J774A.1 cells were cultured in 24-well tissue culture plates at 37° C. with 5% (v/v) $CO_2$ until confluent monolayers of approx. $1 \times 10^6$ cells per well were established. The culture medium was removed from the cells and was replaced with 0.1 ml bacterial suspension at $1 \times 10^8$ CFU/ml. Infected monolayers were incubated as before for 30 minutes to allow bacterial invasion of the cells. The inoculum was aspirated and the monolayer washed with PBS three times. Cells were then overlaid with culture medium containing gentamicin at 10 μg/ml and incubated as before for 30 minutes to kill any remaining extracellular bacteria. The medium was aspirated and the monolayer again washed with PBS three times. Finally the cells were overlaid with maintenance medium containing gentamicin at 2 μg/ml and incubated as before. This was denoted time point 0 hours post-infection. At time points 0, 24, and 48 hours bacteria were recovered from duplicate monolayers by aspiration of the media, washing in PBS, and lysis using sterile water. Cell lysates were decimally diluted in PBS and the number of viable, internalised bacteria was determined by counting the resultant colonies on BCGA. This experiment was repeated in triplicate.

Animal Studies

Groups of 6, 6-8 week old, female Balb/c mice (Charles River, Basingstoke, UK) were dosed by the sub-cutaneous (sc) route with serial dilutions of bacteria in PBS. The concentration of bacteria in the inoculum was determined by retrospective viable count.

TABLE 2

Survival of mice administered with Δggt

| | Δggt Dose (CFU) | | | | | | |
|---|---|---|---|---|---|---|---|
| | 8.75 | 87.5 | $8.75 \times 10^2$ | $8.75 \times 10^3$ | $8.75 \times 10^4$ | $8.75 \times 10^5$ | $8.75 \times 10^6$ |
| No. survivors (out of 6 tested) | 6 | 6 | 5 | 5 | 4 | 6 | 2 |
| Time to humane end-point (days post-inoculation) | n/a | n/a | 11 | 10 | 8, 9 | n/a | 4, 7, 7, 7 |

The results are also represented diagrammatically in FIG. 5. However, the plots for some groups overlay the plots for other groups and therefore on occasions it is difficult to visually distinguish between certain groups.

The potential attenuation of the SCHU S4 mutant strain was also investigated using a murine model of infection. Balb/C mice received doses of SCHU S4 Δggt ranging from 8.75 CFU to $8.75 \times 10^6$ CFU in one-log increments via the sc route. Control mice that received $1.3 \times 10^3$ CFU SCHU S4 had all reached the humane end-point by tour days post-infection. Mice that received SCHU S4 Δggt survived in a dose-dependant manner (table 2 above). The median lethal dose (MLD) of SCHU S4 Δggt was calculated as approx. $2 \times 10^6$ CFU, compared to a wild type *F. tularensis* MLD of approx. 1 CFU. Glutathione provides a source of cysteine essential for intracellular multiplication of *Francisella tularensis*. (PLoS PATH 5:e1000284). Fully virulent strains, such as SCHU S4, display the full effects of mutations in a clinically relevant framework.

Mice surviving the initial challenge were subsequently challenged 49 days later with wild type bacteria to determine whether a protective immune response had been induced (see details below). Humane end-points were strictly observed, and animals deemed incapable of survival were humanely killed by cervical dislocation. The median lethal dose to induce morbidity or death (MLD) is approximately 1 colony forming unit (CFU) for SCHU S4 given by the sc route.

A control group of 6 naïve mice was also challenged with 100 MLD SCHU S4—these all reached the humane end-point by day 5 post-challenge.

This data is also represented diagrammatically in FIG. 6. However, the plots for some groups overlay the plots for other groups and therefore on occasions it is difficult to visually distinguish between certain groups.

Thus the protective efficacy of SCHU S4 Δggt against a wild type challenge was investigated using this murine model of infection. Mice that survived vaccination with SCHU S4 Δggt were subsequently challenged with 100 MLDs SCHU S4. Mice vaccinated with $8.75 \times 10^2$ CFU SCHU S4 Δggt or less did not show total protection, whereas mice that received $8.75 \times 10^3$ CFU SCHU S4 Δggt or more were fully protected (FIG. 6 and Table 3). When taken together these data demonstrate that GGT is required for virulence in *F. tularensis* SCHU S4. Deletion of ggt is attenuating, but when given at sufficiently high doses ($\geq 8.75 \times 103$ CFU) the mutant strain elicits a solid protective immune response against a fully virulent wild type challenge when administered by the sc route.

TABLE 3

Survival of mice administered with Δggt and then challenged with 100 MLD SCHU S4

| DAY POST-CHALLENGE | Survivors (%) per Δggt dose (CFU) | | | | | | |
|---|---|---|---|---|---|---|---|
| | 8.75 | 87.5 | $8.75 \times 10^2$ | $8.75 \times 10^3$ | $8.75 \times 10^4$ | $8.75 \times 10^5$ | $8.75 \times 10^6$ |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 50 | 100 | 100 | 100 | 100 | 100 | 100 |
| 5 | 50 | 100 | 100 | 100 | 100 | 100 | 100 |
| 6 | 50 | 100 | 100 | 100 | 100 | 100 | 100 |
| 7 | 50 | 100 | 100 | 100 | 100 | 100 | 100 |
| 8 | 50 | 100 | 100 | 100 | 100 | 100 | 100 |
| 9 | 50 | 100 | 100 | 100 | 100 | 100 | 100 |
| 10 | 50 | 100 | 100 | 100 | 100 | 100 | 100 |
| 11 | 50 | 100 | 80 | 100 | 100 | 100 | 100 |
| 12 | 50 | 100 | 80 | 100 | 100 | 100 | 100 |
| 13 | 50 | 100 | 80 | 100 | 100 | 100 | 100 |
| 14 | 50 | 100 | 80 | 100 | 100 | 100 | 100 |
| 15 | 33 | 83 | 80 | 100 | 100 | 100 | 100 |
| 16 | 33 | 83 | 80 | 100 | 100 | 100 | 100 |

TABLE 1

| ID | FTN No. | FTT No. | Fold change | $P_{FDR}$ | Annotation |
|---|---|---|---|---|---|
| feoB* | 0066 | 0249 | 3.54 | 0.04 | Ferrous iron transport protein B |
| pilV* | 0413 | 0888 | 1.51 | 0.04 | Type IV pili, pilus assembly protein |
| FTN_1125* | 1125 | 1144$^c$ | 1.46 | 0.04 | Short-chain dehydrogenase |
| lysA* | 1530 | 0027 | 4.91 | 0.05 | Diaminopimelate decarboxylase |
| FTN_1685* | 1685 | 0026 | 7.55 | 0.04 | Drug H$^+$ antiporter-1 (DHA1) family protein |
| dnaN* | 0002 | 0002 | 1.67 | 0.04 | DNA polymerase III, beta subunit |
| pyrF** | 0035 | 1648 | 1.47 | 0.05 | Orotidine-5'-phosphate decarboxylase |
| ostA2* | 0713 | 0740 | 1.55 | 0.04 | Organic solvent tolerance protein OstA |
| FTN_0753* | 0753 | 0580 | 1.50 | 0.05 | Hypothetical protein |
| FTN_0755* | 0755 | 0582 | 1.67 | 0.03 | 4Fe—4S Ferredoxin |
| sufB* | 0851 | 0971 | 2.77 | 0.04 | SufS activator complex, SufB subunit |
| ggt* | 1159 | 1181 | 1.61 | 0.04 | Gamma-glutamyltranspeptidase |
| FTN_1169* | 1169 | 1191 | 1.47 | 0.04 | Peptidase M20 family |
| bfr* | 1410 | 1441 | 1.76 | 0.05 | Bacterioferritin |
| lysA* | 1530 | 0027 | 8.24 | 0.04 | Diaminopimelate decarboxylase |
| FTN_0979* | 0979 | 0536 | 2.45 | 0.05 | MFS transport protein |
| pyrD* | 0036 | 1647 | 1.65 | 0.05 | Dihydroorotate dehydrogenase |
| FTN_0362* | 0362 | 0847 | 1.47 | 0.05 | Deoxyribodipyrimidine photolyase-related protein |
| FTN_0721* | 0721 | 0749 | 1.46 | 0.05 | Hypothetical protein |
| coaD* | 0754 | 0581 | 1.45 | 0.04 | Phosphopantetheine adenylyltransferase |
| sufB* | 0851 | 0971 | 4.97 | 0.04 | SufS activator complex, SufB subunit |
| rubA* | 1084 | 0595 | 1.51 | 0.04 | Rubredoxin |
| FTN_1612* | 1612 | 0103 | 1.48 | 0.05 | Hypothetical protein |
| frgA* | 1682 | 0029 | 9.60 | 0.04 | Siderophore biosynthesis protein |
| FTN_1683* | 1683 | 0028 | 3.82 | 0.05 | Drug H$^+$ antiporter-1 (DHA1) family protein |
| trpB* | 1739 | 1773 | 1.64 | 0.05 | Tryptophan synthase beta chain |
| PpdK$^+$ | 0064 | 0250 | 8.31 | 0.04 | Phosphoenolpyruvate synthase/pyruvate phosphate dikinase |
| FTN_0312$^+$ | 0312 | 1618$^c$ | 6.74 | 0.05 | Drug H+ antiporter-1 (DHA1) family protein |
| glyQ$^+$ | 0519 | 0419 | 3.32 | 0.05 | Glycyl-tRNA synthetase alpha chain |
| FTN_0990$^+$ | 0990 | 0516$^c$ | 2.74 | 0.04 | 4Fe—4S Ferredoxin, FAD-dependent |
| ptsN$^+$ | 1295 | 1280 | 7.02 | 0.05 | PEP-dependent sugar phosphotransferase system (PTS), enzyme IIA |
| rnfB$^+$ | 1034 | 0649 | 2.77 | 0.04 | Iron-sulfur cluster-binding protein |
| thrS$^+$ | 1191 | 1817 | 1.55 | 0.04 | Threonyl-tRNA synthetase |
| FTN_1542$^+$ | 1542 | 1693 | 1.57 | 0.04 | Hypothetical protein |
| FTN_1326• | 1326 | 1361$^c$ | 24.88 | 0.04 | Hypothetical protein |
| FTN_0859• | 0859 | 0978 | 2.90 | 0.01 | Hypothetical membrane protein |
| FTN_0049• | 0049 | 1068 | 4.86 | 0.05 | Hypothetical protein |
| galU• | 0729 | 0757 | 2.78 | 0.05 | UTP-glucose-1-phosphate uridylyltransferase |
| dxs | 0896 | 018c | 10.39 | 0.03 | 1-deoxy-D-xylulose 5-phosphate synthase |
| FTN_1010• | 1010 | 0672$^c$ | 4.53 | 0.05 | MFS transport protein |
| FTN_1053• | 1053 | 0628 | 6.28 | 0.05 | Outer membrane protein of unknown function |
| FTN_1068• | 1068 | 0613 | 11.39 | 0.05 | Hypothetical protein |
| ispF• | 1110 | 1128 | 5.87 | 0.05 | 2-C-methyl-D-erythritol 2,4-cyclodiphosphate synthase |
| feoA | 1368 | 1403 | | | Fe2+ transport system protein A |
| sdhC | 1639 | 0072 | | | Succinate dehydrogenase, cytochrome b556 |
| nuoA | 1680 | 0031 | | | NADH dehydrogenase I, A subunit |
| FTN_1068† | 1068 | 0613 | 1.56 | 0.05 | Hypothetical protein |
| fabH† | 1337 | 1373 | 1.48 | 0.03 | 3-oxoacyl-[acyl-carrier protein] synthase III |
| FTN_0588† | 0588 | 0497$^c$ | 1.45 | 0.05 | Asparaginase |
| FTN_1345† | 1345 | 1381$^c$ | 1.45 | 0.05 | Hypothetical protein |

•Heat stress
*Iron starvation
†Acid stress
Other

The invention claimed is:

1. An attenuated *Francisella* mutant bacterium, wherein the gene gamma-glutamyl transpeptidase (ggt) is deleted.

2. The attenuated *Francisella* mutant bacterium of claim 1, wherein the attenuated *Francisella* mutant bacterium is attenuated *Francisella tularensis*.

3. The attenuated *Francisella* mutant bacterium of claim 1, wherein the attenuated *Francisella* mutant bacterium is attenuated *Francisella tularensis*.

4. The attenuated *Francisella* mutant bacterium of claim 1, wherein the attenuated *Francisella* mutant bacterium is derived from SCHU S4 strain of *Francisella tularensis* tularensis.

5. The attenuated *Francisella* mutant bacterium of claim 1, wherein a further gene of the bacterium is deleted or silenced.

6. The attenuated *Francisella* mutant bacterium of claim 5, wherein the silenced or the deleted further gene is the ferrous iron transport protein B (feoB) gene.

7. A pharmaceutical composition comprising the attenuated *Francisella* mutant bacterium of claim 4 and a pharmaceutically acceptable carrier.

8. The pharmaceutical composition of claim 7, wherein the pharmaceutical composition is a vaccine composition.

9. A method of preparing the attenuated *Francisella* mutant bacterium of claim 1, comprising deleting the ggt gene in a wild-type *Francisella* bacterium.

10. The method of claim 9, further comprising deleting or silencing a further gene of the bacterium.

11. The attenuated *Francisella* mutant bacterium obtained by the method of claim 1.

12. A method of formulating a composition comprising an attenuated *Francisella* mutant having at least the deleted ggt gene, the method comprising:
    culturing the attenuated *Francisella* mutant having at least the deleted ggt gene and
    admixing the cultured attenuated *Francisella* mutant with a pharmaceutically acceptable excipient.

13. The method of claim 12, wherein the culturing is performed in a culture medium and at a temperature suitable for growth of the attenuated *Francisella* mutant.

14. The method of claim 13, wherein the culture medium is blood cysteine glucose agar (BCGA).

15. The method of claim 14, wherein the temperature is about 37° C.

16. The attenuated *Francisella* mutant bacterium of claim 1, wherein the attenuated *Francisella* mutant bacterium is 1,000,000 or more times less virulent than the corresponding wild-type *Francisella* bacterium.

17. The attenuated *Francisella* mutant bacterium of claim 6, wherein the attenuated *Francisella* mutant bacterium is 1,000,000 or more times less virulent than the corresponding wild-type *Francisella* bacterium.

18. A composition comprising the attenuated *Francisella* mutant bacterium of claim 1 and a pharmaceutically acceptable carrier.

* * * * *

UNITED STATES PATENT AND TRADEMARK OFFICE
CERTIFICATE OF CORRECTION

PATENT NO. : 8,609,108 B2  
APPLICATION NO. : 13/264175  
DATED : December 17, 2013  
INVENTOR(S) : Helen Le Butt, Phillip Matthew Ireland and Petra Claire Farquar Oyston Page 1 of 1

It is certified that error appears in the above-identified patent and that said Letters Patent is hereby corrected as shown below:

In the Claims

Column 23, Claim 3, Line 38  
Insert --tularensis-- following the word *tularensis*

Column 23, Claim 4, Line 41  
Delete the second occurrence of the word "tularensis"

Column 24, Claim 11, Line 31  
Delete "1" and insert --9-- in place thereof

Signed and Sealed this  
Twenty-seventh Day of May, 2014

Michelle K. Lee  
*Deputy Director of the United States Patent and Trademark Office*

SEQUENCE LISTING

<160> NUMBER OF SEQ ID NOS: 10

<210> SEQ ID NO 1
<211> LENGTH: 20
<212> TYPE: DNA
<213> ORGANISM: Artificial sequence
<220> FEATURE:
<223> OTHER INFORMATION: Synthetic sequence: Oligonucleotide

<400> SEQUENCE: 1

```
tccatgacgt tcctgacgtt                                              20

<210> SEQ ID NO 2
<211> LENGTH: 18
<212> TYPE: DNA
<213> ORGANISM: Artificial sequence
<220> FEATURE:
<223> OTHER INFORMATION: Synthetic sequence: Oligonucleotide

<400> SEQUENCE: 2
tctcccagcg tgcgccat                                                18

<210> SEQ ID NO 3
<211> LENGTH: 30
<212> TYPE: DNA
<213> ORGANISM: Artificial sequence
<220> FEATURE:
<223> OTHER INFORMATION: Synthetic sequence: Oligonucleotide

<400> SEQUENCE: 3
accgatgacg tcgccggtga cggcaccacg                                   30

<210> SEQ ID NO 4
<211> LENGTH: 24
<212> TYPE: DNA
<213> ORGANISM: Artificial sequence
<220> FEATURE:
<223> OTHER INFORMATION: Synthetic sequence: Oligonucleotide

<400> SEQUENCE: 4
tcgtcgtttt gtcgttttgt cgtt                                         24

<210> SEQ ID NO 5
<211> LENGTH: 20
<212> TYPE: DNA
<213> ORGANISM: Artificial sequence
<220> FEATURE:
<223> OTHER INFORMATION: Synthetic sequence: Oligonucleotide

<400> SEQUENCE: 5
tccatgacgt tcctgatgct                                              20

<210> SEQ ID NO 6
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 6
tcgacgtttt cggcgcgcgc cg                                           22

<210> SEQ ID NO 7
<211> LENGTH: 26
<212> TYPE: DNA
<213> ORGANISM: Artificial sequence
<220> FEATURE:
<223> OTHER INFORMATION: Synthetic sequence: left flank forward primer,
      ggtF1

<400> SEQUENCE: 7
acgcgttagg ttaccttggg cttgag                                       26

<210> SEQ ID NO 8
<211> LENGTH: 27
<212> TYPE: DNA
<213> ORGANISM: Artificial sequence
```

```
-continued

<220> FEATURE:
<223> OTHER INFORMATION: Synthetic sequence: reverse primer, ggtR1

<400> SEQUENCE: 8
agatctggtt attaaacact ttaatag                                             27

<210> SEQ ID NO 9
<211> LENGTH: 24
<212> TYPE: DNA
<213> ORGANISM: Artificial sequence
<220> FEATURE:
<223> OTHER INFORMATION: Synthetic sequence: right flank forward primer,
      ggtF2

<400> SEQUENCE: 9
agatctacga cgcattaaag aaac                                                24

<210> SEQ ID NO 10
<211> LENGTH: 27
<212> TYPE: DNA
<213> ORGANISM: Artificial sequence
<220> FEATURE:
<223> OTHER INFORMATION: Synthetic sequence: reverse primer, ggtR2

<400> SEQUENCE: 10
acgcgttgtg ggattaagtg ggaaacc                                             27
```